US006803218B1

(12) United States Patent
Seyfried et al.

(10) Patent No.: US 6,803,218 B1
(45) Date of Patent: Oct. 12, 2004

(54) ENZYMES WHICH DEHYDRATE GLYCEROL

(75) Inventors: Markus Seyfried, Silver Springs, MD (US); Juergen Wiegel, Athens, GA (US); Gregory Whited, Belmont, CA (US)

(73) Assignee: Genencor Intl., Inc., Rochester, NY (US)

( * ) Notice: Subject to any disclaimer, the term of this patent is extended or adjusted under 35 U.S.C. 154(b) by 0 days.

(21) Appl. No.: 09/405,692

(22) Filed: Sep. 24, 1999

(51) Int. Cl.$^7$ ................................................. C12P 7/18
(52) U.S. Cl. ........................................................ 435/158
(58) Field of Search .............................. 435/157, 158, 435/252.1; 528/276

(56) References Cited

U.S. PATENT DOCUMENTS

| | | | |
|---|---|---|---|
| 4,778,760 A | * 10/1988 | Ishida et al. ................ | 435/202 |
| 5,008,473 A | 4/1991 | Breitkopf et al. ........... | 568/868 |
| 5,340,909 A | * 8/1994 | Doerr et al. ................. | 528/276 |
| 5,356,812 A | 10/1994 | Matsuyama et al. ........ | 435/280 |
| 5,599,689 A | 2/1997 | Haynie et al. ................ | 435/42 |
| 5,650,148 A | 7/1997 | Gage et al. ................. | 424/93.2 |
| 5,686,276 A | * 11/1997 | Laffend et al. ............. | 435/158 |
| 5,872,204 A | 2/1999 | Kuo et al. ................... | 528/279 |
| 6,013,494 A | 1/2000 | Nakamura et al. .......... | 435/158 |

FOREIGN PATENT DOCUMENTS

| | | |
|---|---|---|
| WO | WO 98/21339 | 5/1998 |
| WO | WO 98/21340 | 5/1998 |
| WO | WO 98/21341 | 5/1998 |

OTHER PUBLICATIONS

Hartley et al. "Industrial prospects for thermophiles and thermophilic enzymes", (1983) Biochem Soc Symp 48:133–146.*
Vieille et al. "Thermozymes", (1996) Biotechnol Annu Rev 2:1–83.*
Slobodkin et al. "Isolation and characterization of the homoacetogenic thermophilic bacterium Moorella glycerini sp nov", (1997) Int J Syst Bacteriol 47:969–974.*
Demain et al. "Anaerobic Fermentations" in Manual of Industrial Microbiology and Biotechnology, 2nd Ed., 1999, American Society for Microbiology, Washington, DC.*
Altschul et al. "*Gapped Blast and PSI–Blast: A New Generation Of Protein Database Search Programs,*" Nucleic Acids Research, 1997, vol. 5, No. 17, pp 3389–3402.
Altschul et al. "*Basic Local Alignment Search Tool,*" J. Mol. Biol. (1990), 215, pp 403–410.
Benton et al. "*Screening λgt Recombinant Clones By Hybridization To Single Plaques In Situ,*" Science, vol. 196, Apr. 1977, pp 180–182.
Brock, Thomas D. "*Thermophiles,*" General, Molecular, And Applied Microbiology, A Wiley–Interscience Publication, John Wiley & Sons, New York, pp 18–37. (1986).

Cameron et al., "*Metabolic Engineering Of Propanediol Pathways,*" Biotechnol. Prog. 1998, vol. 14, pp 116–125.
Daniel et al. "*Purification of 1,3–Propanediol Dehydrogenase From Citrobacter Freundii and Cloning, Sequencing, and Overexpression Of The Corresponding Gene In Escherichia coli,*" Journal Of Bacteriology, Apr. 1995, vol. 177, No. 8, pp 2151–2156.
Deshpande, Mukund V. "*Ethanol Production From Cellulose By Coupled Saccharification/Fermentation Using Saccharomyces cerevisiae And Cellulase Complex From Sclerotium rolfsii UV–8 Mutant*,*" Applied Biochemistry And Biotechnology, vol. 36, 1992, pp 227–234.
Grunstein et al. "*Colony Hybridization: A Method For The Isolation Of Cloned DNAs That Contain A Specific Gene,*" Proc. Nat. Acad. Sci, USA, vol. 72, No. 10, Oct. 1975, pp 3961–3965.
Honda et al. "*In Situ Reactivation Of Glycerol–Inactivated Coenzyme B12–Dependent Enzymes, Glycerol Dehydratase and Diol Dehydratase,*" Journal Of Bacteriology, Sep. 1980, vol. 143, No. 3, pp 1458–1465.
Johnson E. A. "*Klebsiella pneumoniae 1,3–Propanediol: NAD+ Oxidoreductase,*" Journal Of Bacteriology, May 1987, vol. 169, No. 5, pp 2050–2054.
Kaufman, Randal J. "*Selection And Coamplification of Heterologous Genes In Mammalian Cells,*" Methods In Enzymology, vol. 185, pp 537–566. (1990).
Luers et al. "*Glycerol Conversion to 1,3–Propanediol By Clostridium pasteurianum: Cloning And Expression Of The Gene Encoding 1,3–Propanediol Dehydrogenase,*" FEMS Microbiology Letters 154 (1997) pp 337–345.
Macis et al. "*Properties and Sequence of the Coenzyme B12–Dependent Glycerol Dehydratase of Clostridium pasteurianum,*" FEMS Microbiology Letters164 (1998), pp 21–28.
Poppe et al. "*Kinetic Investigations With Inhibitors That Mimic The Posthomolysis Intermediate In The Reactions Of Coenzyme–B12–Dependent Glycerol Dehydratase And Diol Dehydratase,*" European Journal of Biochemistry, vol. 245, 1997, pp 398–401.
Seyfried et al. "*Cloning, Sequencing, And Overexpression Of The Genes Encoding Coenzyme B12–Dependent Glycerol Dehydratase Of Citrobacter freundii,*" Journal Of Bacteriology, vol. 178, No. 19, Oct. 1996, pp 5793–5796.

(List continued on next page.)

Primary Examiner—Rebecca E. Prouty
Assistant Examiner—David Steadman
(74) Attorney, Agent, or Firm—Richard T. Ito; Genencor Intl , Inc.

(57) ABSTRACT

The present invention relates to improved methods and reagents for the production of 1,3-propanediol. In particular, the present invention provides novel thermophilic organisms and thermostable enzymes cable of catalyzing the fermentation of glycerol to 1,3-propanediol. The present invention also relates to methods of isolating such thermophilic organisms, methods of cloning polynucleotides that encode such enzymes, polynucleotides encoding such enzymes, and methods of using such enzymes and organisms for the production of 1,3-propanediol.

19 Claims, 5 Drawing Sheets

OTHER PUBLICATIONS

Shilo et al. *"DNA Sequences Homologous To Vertebrate Oncogenes Are Conserved In Drosophila Melanogaster,"* Proc. Natl. Acad. Sci. USA, vol. 78, No. 11, Nov. 1981, pp 6789–6792.

Takamasa et al. *"Identification And Expression Of The Genes Encoding A Reactivating Factor For Adenosylcobalamin–Dependent Glycerol Dehydratase,"* Journal Of Bacteriology, vol. 181, No. 13, Jul. 1999, pp 4110–4113.

Takamasa et al. *"Cloning, Sequencing, And High Level Expression Of The Genes Encoding Adenosylcobalamin–Dependent Glycerol Dehydrase Of Klebsiella pneumoniae\*,"* The Journal Of Biological Chemistry, vol. 271, No. 37, Sep. 13, 1996, pp 22352–22357.

Tong et al. *"1,3–Propanediol Production By Escherichia coli Expressing Genes from the Klebsiella pneumoniae dha regulon,"* Applied And Environmental Microbiology, Dec. 1991, vol. 57, No. 12, pp 3541–3546.

\* cited by examiner

TIME COURSE ASSAY FOR THE CONVERSION OF GLYCEROL TO 3-HPA BY ANAEROBICALLY TOLUENIZED JW/MS-VS-5 CELLS AT 60 °C UNDER ANAEROBIC CONDITIONS

TIME COURSE ASSAY FOR THE
CONVERSION OF 1,2-PROPANEDIOL TO PROPIONALDEHYDE BY ANAEROBICALLY
TOLUENIZED JW/MS-VS-5 CELLS AT 60 °C UNDER ANAEROBIC CONDITIONS

SEQUENCE LISTING

```
<160> NUMBER OF SEQ ID NOS:  8

<210> SEQ ID NO 1
<211> LENGTH: 35
<212> TYPE: DNA
<213> ORGANISM: Artificial Sequence
<220> FEATURE:
<223> OTHER INFORMATION: Primer

<400> SEQUENCE: 1
ggaattcaga tctcagcaat gaaaagatca aaacg                                   35

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
gggctgtggt aacttattag atctcg                                             26

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
ggaatacaga tctcagcaat gcaacagaca accc                                    34

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
gctgaatcat tccctcacta gatctcg                                            27
```

-continued

```
<210> SEQ ID NO 5
<211> LENGTH: 37
<212> TYPE: DNA
<213> ORGANISM: Artificial Sequence
<220> FEATURE:
<223> OTHER INFORMATION: Primer

<400> SEQUENCE: 5
ggaattcaga tctcagcaat gagcgagaaa accatgc                    37

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
cgacgcattt ccttcgatta gatctcg                                27

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
aggtggtgcg gatcctgtcg aatccta                                28

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
gacgatgacc ggccagtccg cttaatttct agagcatag                  39
```

ENZYMES WHICH DEHYDRATE GLYCEROL

FIELD OF THE INVENTION

The present invention relates to improved methods and reagents for the production of 1,3-propanediol. In particular, the present invention provides novel thermophilic organisms and thermostable enzymes capable of catalyzing the fermentation of glycerol to 1,3-propanediol. The present invention also relates to methods of isolating such thermophilic organisms, methods of cloning polynucleotides that encode such enzymes, polynucleotides encoding such enzymes, and methods of using such enzymes and organisms for the production of 1,3-propanediol.

BACKGROUND 1,3-Propanediol is a monomer used in the production of polyester fibers and the manufacture of polyurethanes and cyclic compounds.

A variety of synthetic routes to 1,3-propanediol are known. For example, 1,3-propanediol can be synthesized: (1) by the conversion of ethylene oxide over a catalyst in the presence of phosphine, water, carbon monoxide, hydrogen and an acid; (2) by the catalytic solution phase hydration of acrolein, followed by reduction; or (3) by reacting a hydrocarbon (e.g., glycerol) in the presence of carbon monoxide and hydrogen over catalysts having atoms from group VIII of the periodic table. However, traditional chemical synthesis methods are expensive and generate waste streams containing environmental pollutants, and are thus far from ideal. It would be desirable to develop alternate methods and reagents for the production of 1,3-propanediol that are less expensive and more environmentally friendly.

An alternate approach is to use enzymes, either in vivo (i.e., in a microorganism) or in vitro, to catalyze the fermentation of glycerol to 1,3-propanediol. See, e.g., WO 98/21339, WO 98/21341, and U.S. Pat. Nos. 5,821,092, 5,254,467, 5,633,362 and 5,686,276. Bacterial strains able to produce 1,3-propanediol from glycerol have been found, for example, in the groups Citrobacter, Clostridium, Enterobacter, Ilyobacter, Klebsiella, Lactobacillus, and Pelobacter. These bacteria convert glycerol to 1,3-propanediol by means of a two step, enzyme catalyzed reaction. In the first step, a dehydratase catalyzes the conversion of glycerol to 3-hydroxypropionaldehyde (3-HP) and water (Equation 1). In the second step, 3-HP is reduced to 1,3-propanediol by a NAD$^+$-linked oxidoreductase (Equation 2).

Glycerol→3-HP+H$_2$O           (Equation 1)

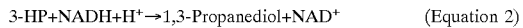

3-HP+NADH+H$^+$→1,3-Propanediol+NAD$^+$     (Equation 2)

The 1,3-propanediol is not metabolized further and, as a result, can accumulate in the media to a high concentration. The overall reaction results in the oxidation of reduced b-nicotinamide adenine dinucleotide (NADH) to nicotinamide adenine dinucleotide (NAD$^+$).

The bioconversion of glycerol to 1,3-propanediol is generally performed under anaerobic conditions using glycerol as the sole carbon source and in the absence of other exogenous reducing equivalent acceptors. In some bacterial strains, e.g., certain strains of Citrobacter, Clostridium, and Klebsiella, a parallel pathway for glycerol metabolism operates which first involves oxidation of glycerol to dihydroxyacetone (DHA) by a NAD$^+$- (or NADP$^+$-) linked glycerol dehydrogenase (Equation 3). The DHA, following phosphorylation to dihydroxyacetone phosphate (DHAP) by a DHA kinase (Equation 4), becomes available for biosynthesis and for supporting ATP generation via, for example, glycolysis.

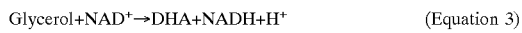

Glycerol+NAD$^+$→DHA+NADH+H$^+$     (Equation 3)

DHA+ATP→DHAP+ADP     (Equation 4)

In contrast to the 1,3-propanediol pathway, this pathway may provide carbon and energy to the cell and produces rather than consumes NADH.

In *Klebsiella pneumoniae* and *Citrobacter freundii*, the genes encoding the functionally linked activities of glycerol dehydratase (dhaBCE), 1,3-propanediol oxidoreductase (dhaT), glycerol dehydrogenase (dhaD), and dihydroxyacetone kinase (dhaK) are found in the dha regulon. The dha regulons from Citrobacter and Klebsiella have been expressed in *Escherichia coli* and have been shown to convert glycerol to 1,3-propanediol (Tong et al., *Appl. Environ. Microbiol.* 57:3541–46 (1991); Seyfried et al., *J. of Bact.* 178:5793–96 (1996); Tobimatsu et al., *J. Biol. Chem.* 271:22352–22357 (1996)).

In view of the potential advantages inherent in the use of biological methods and reagents to produce 1,3-propanediol, their exists a need for the development and identification of novel microorganisms and enzymes capable of converting glycerol and other carbon substrates to 1,3-propanediol having superior characteristics. The present invention satisfies that need by providing superior microorganisms and enzymes, along with methods of identifying other superior microorganisms and enzymes.

SUMMARY OF THE INVENTION

The present invention relates to improved methods and reagents for the production of 1,3-propanediol. In particular, the present invention provides novel thermophilic organisms and thermostable enzymes capable of catalyzing the fermentation of glycerol to 1,3-propanediol. The present invention also relates to methods of isolating such thermophilic organisms, methods of cloning polynucleotides that encode such enzymes, polynucleotides encoding such enzymes, and methods of using such enzymes and organisms for the production of 1,3-propanediol.

In one aspect, the invention provides a method of converting glycerol to 1,3-propanediol in a thermophilic organism, the method comprising: providing a thermophilic organism that ferments glycerol to 1,3-propanediol; and culturing the thermophilic organism under conditions such that 1,3-propanediol is produced. In a preferred embodiment, the method further comprises the step of collecting 1,3-propanediol produced by the thermophilic organism. In another preferred embodiment, the thermophilic organism is *Caloramator viterbiensis*, wherein a thermophilic organism derived from the organism deposited as ATCC designation PTA-584 is particularly preferred.

The invention further provides a method of producing 1,3-propanediol from glycerol, the method comprising: incubating glycerol with a thermostable dehydratase enzyme, thereby converting the glycerol to 3-hydroxypropionaldehyde; and reducing the 3-hydroxypropionaldehyde to 1,3-propanediol. In a preferred embodiment, the reduction of the 3-hydroxypropionaldehyde to 1,3-propanediol is catalyzed by a thermostable 1,3-propanediol oxidoreductase. In another preferred embodiment, the method further comprises the step of collecting 1,3-propanediol. In yet another preferred embodiment, thermostable dehydratase enzyme is derived from a thermophilic organism such as *Caloramator viterbiensis*, wherein a thermophilic organism derived from the organism deposited as ATCC designation PTA-584 is particularly preferred.

Still another aspect of the invention provides an isolated thermostable glycerol fermentation enzyme that is derived from *C. viterbiensis*, wherein a thermostable glycerol fermentation enzyme derived from the organism deposited as ATCC designation PTA-584 is particularly preferred. In particular preferred embodiments, the thermostable glycerol fermentation enzyme is a dehydratase, such as glycerol dehydratase, or a NAD$^+$-linked oxidoreductase, such as 1,3-propanediol oxidoreductase. The invention also provides an isolated thermostable glycerol fermentation enzyme that is homologous to a thermostable glycerol fermentation enzyme derived from *C. viterbiensis*.

Also provided by the invention is an isolated culture or cell of *C. viterbiensis*. In a non-limiting embodiment, the genome of the culture or cell is at least 85% identical to the genome of the organisms deposited as ATCC designation PTA-584, preferably 90% identical to the genome of the organisms deposited as ATCC designation PTA-584, more preferably 95% identical to the genome of the organisms deposited as ATCC designation PTA-584, and most preferably at least 99% identical to the genome of the organisms deposited as ATCC designation PTA-584. In another non-limiting embodiment, the 16S rDNA sequence of the culture or cell is at least 95% identical to the 16S rDNA sequence of the organisms deposited as ATCC designation PTA-584, and preferably at least 98% identical to the 16S rDNA sequence of the organisms deposited as ATCC designation PTA584.

In another aspect, the present invention provides a method of cloning a polynucleotide sequence that encodes a thermostable glycerol fermentation enzyme, the method comprising: hybridizing polynucleotide probes homologous to a portion of a known glycerol fermentation enzyme gene to a polynucleotide molecule from an environmental sample suspected of containing a thermophilic organism; and isolating a polynucleotide sequence that binds to at least one polynucleotide probe. In a non-limiting embodiment, the method uses a polymerase chain reaction to amplify the polynucleotide sequence that binds to the polynucleotide probes. In a preferred embodiment, the thermostable glycerol fermentation enzyme is derived from a thermophilic organism identified as fermenting glycerol to 1,3-propanediol, wherein *C. viterbiensis* is particularly preferred. In another preferred embodiment, the polynucleotide probes are homologous to a portion of a known dhaB gene, wherein probes homologous to the dhaB gene from Klebsiella are particularly preferred.

The invention further provides a method of cloning a polynucleotide sequence that encodes a thermostable glycerol fermentation enzyme, the method comprising: transforming a target organism that cannot grow anaerobically on glycerol with DNA from a thermophilic organism; and identifying those transformed target organisms that contain the polynucleotide sequence that encodes an enzyme that ferments glycerol to 1,3-propanediol by their anaerobic growth on glycerol. In a non-limiting embodiment, the thermostable glycerol fermentation enzyme is derived from a thermophilic organism identified as fermenting glycerol to 1,3-propanediol, such as *C. viterbiensis*, wherein a thermophilic organism derived from the organism deposited as ATCC designation PTA-584 is particularly preferred.

Still another aspect of the invention provides a method of isolating a thermophilic organism that catalyzes the fermentation of glycerol to 1,3-propanediol, the method comprising: incubating a sample containing thermophilic organisms in media containing glycerol as the primary carbon source; and isolating at least one thermophilic organism that ferments glycerol into 1,3-propanediol. In non-limiting embodiments, the sample is incubated at a temperature in the range of about 40° C. to about 100° C. and/or under anaerobic conditions. In another non-limiting embodiment, the sample is obtained from a natural source having a temperature of between about ambient to about 100° C., and more preferably from about 50° to about 100° C. In a preferred embodiment, the method further comprises the step of detecting production of 1,3-propanediol and/or acetate by the thermophilic organism.

DETAILED DESCRIPTION OF THE INVENTION

Figure 1:
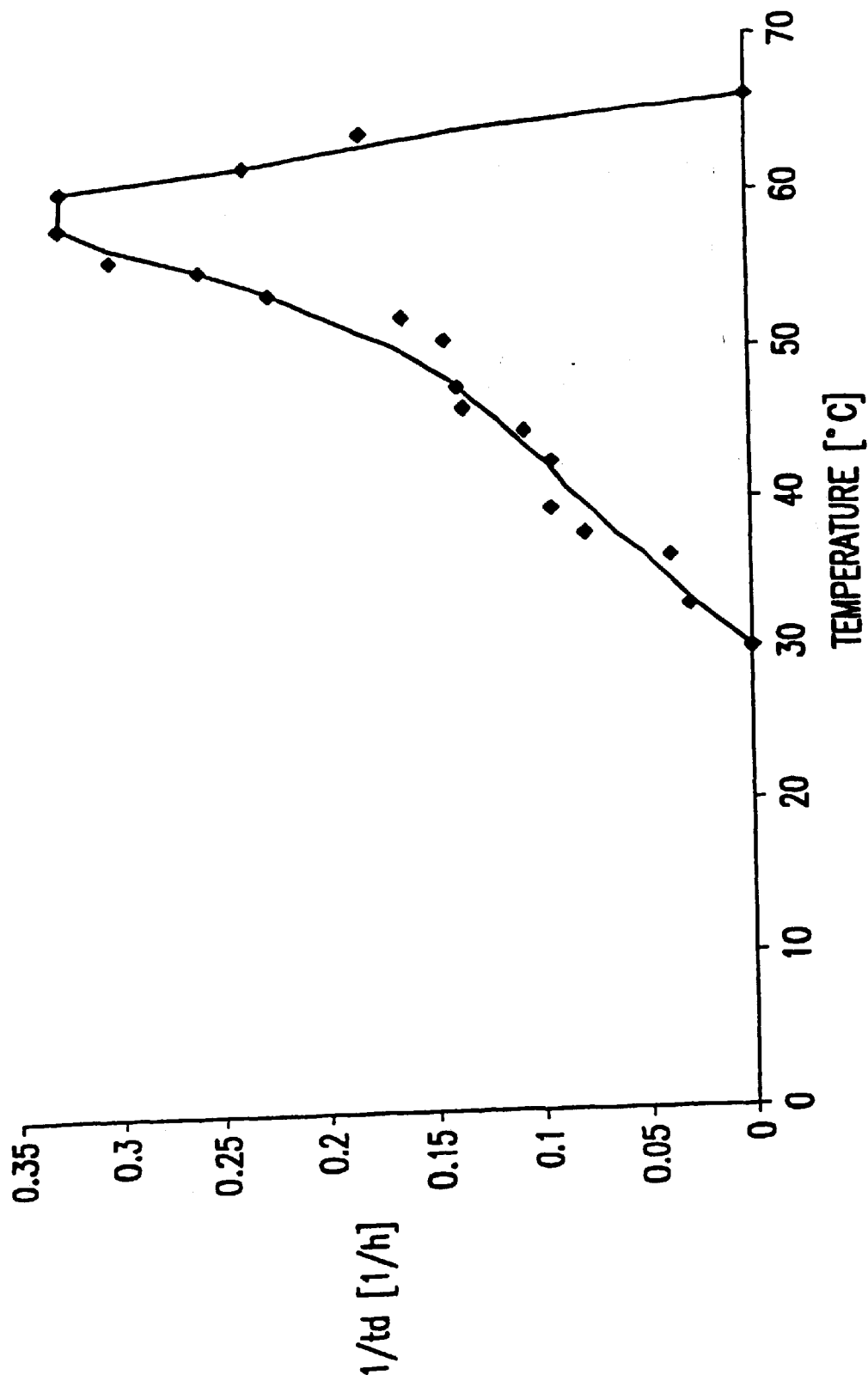
FIG. 1 shows the effect of temperature on growth of strain JW/MS-VS-5, td=doubling time.

Thermophilic organisms are organisms that can survive and grow at elevated temperatures where most other organisms (e.g., mesophiles) would not be able to survive. This unusual resilience towards high temperatures results in part from these organisms' use of thermostable enzymes to catalyze the biological reactions of life. Thermostable enzymes allow thermophilic organisms to catalyze metabolic reactions at elevated temperatures. Such organisms can be isolated from ambient temperature environments, but are more likely isolated from high temperature environments including, for example, hot springs, thermal vents and laundromat effluents. The unusual thermostability of thermophilic bacteria and enzymes allows one to catalyze economically valuable bioconversions at higher temperatures than could be achieved using mesophilic organisms and enzymes. In many cases, thermophilic bacteria are used to catalyze the desired reaction in vivo in a fermentation process. Alternatively, thermostable enzymes can be used to catalyze in in vitro or "cell-free" bioconversions, typically by means of enzymes that have been immobilized to facilitate control of the reaction and recovery of the reaction product.

A number of advantages can be achieved by performing bioconversions at elevated temperatures. As is the case with any chemical reaction, the rates of enzymatically catalyzed reactions generally increase dramatically with an increase in the temperature of the reaction. Obvious efficiency benefits are derived from increasing the rate at which an industrial bioconversion proceeds. In addition, it is possible to prevent microbial contamination of a reaction medium by running the reaction at an elevated temperature where most potential contaminating organisms are unable to survive.

Another advantage of using a thermophilic organism to catalyze a bioconversion at high temperatures is that in some cases the high temperature facilitates the separation and isolation of the desired product from the reaction medium. For example, U.S. Pat. No. 5,182,199 describes the use of thermostable enzymes and high temperature fermentation to facilitate the separation of ethanol from a reaction medium.

Beyond being stable towards high temperatures, thermostable enzymes are also generally found to possess enhanced stability toward other conditions and substances that normally inactivate enzymes. Thermostable enzymes also tend to have a longer storage life than enzymes derived from a mesophilic organism. The present invention provides improved methods and reagents for the enzyme-catalyzed production of 1,3-propanediol. In part, the present invention provides, for the first time, thermophilic organisms and thermostable enzymes capable of catalyzing the fermentation of glycerol into 1,3-propanediol. One novel characteristic of these organisms and enzymes is their ability to remain viable and catalytically active at elevated temperatures, temperatures at which previously identified 1,3-propanediol producing organisms and enzymes are rapidly inactivated. The methods and compositions of the invention can be used to biologically convert glycerol to 1,3-propanediol at elevated temperatures, thereby providing significant advantages over previously described methods, particularly methods conducted at lower temperatures. The present invention further includes methods of identifying thermophilic organisms capable of producing 1,3-propanediol from glycerol, as well as methods of cloning polynucleotides that encode thermostable enzymes that catalyze this conversion.

Thermophilic Organisms Capable of Fermenting Glycerol to 1,3-Propanediol at Elevated Temperatures, and Methods of Isolating Such Organisms In one embodiment, the instant invention provides a thermophilic organism capable of fermenting glycerol to 1,3-propanediol at elevated temperatures.

As used herein, the term "thermophilic organism" refers to an organism capable of growing at a high temperature, preferably at temperatures higher than 50° C., more preferably at temperatures higher than 60° C., still more preferably at temperatures higher than 70° C., and most preferably at temperatures higher than 85° C. Organisms that are capable of growth at temperatures higher than 85° C. are called hyperthermophilic organisms. Examples of thermophilic organisms can be found, for instance, among the prokaryotic microorganisms eubacteria and archaebacteria. Such organisms inhabit, and can be isolated from, hot environments such as hot springs, volcanic areas, and submarine thermal vents. In addition, thermophilic organisms can be isolated from sources at ambient temperatures.

In a preferred embodiment of the invention, the thermophilic organism capable of fermenting glycerol to 1,3-propanediol at elevated temperatures is a strain of *Caloramator viterbiensis*. *C. viterbiensis* is a species of thermophilic bacteria capable of fermenting glycerol to 1,3-propanediol and acetate. *C. viterbiensis* is defined herein as a bacterial species possessing the following identifying characteristics: the species is (1) thermophilic; (2) capable of fermenting glycerol to 1,3-propanediol; and (3) shares "substantial genomic sequence identity" with the type strain JW/MS-VS5$^T$, deposited as ATCC designation PTA-584.

In a non-limiting embodiment of the invention, a member of the species *C. viterbiensis* will also share the following identifying characteristics of type strain JW/MS-VS5$^T$. JW/MS-VS5$^T$ cells are straight to slightly curved rods, 0.4 to 0.6 µm in dimension. Cells occur singly and stain Gram positive. The temperature range for growth at pH 6.0 is 33–64° C., the optimum at 58° C. The pH$^{25C}$ range for growth is from 5.0 to 7.6, with an optimum at 6.0–6.5. Growth is observed with glycerol, glucose, fructose, mannose, galactose, sucrose, cellobiose, lactose, starch, and yeast extract. The strain does not appreciably ferment xylose, arabinose, acetate, lactate, formate, methanol, ethanol, n-propanol, i-propanol, n-butanol, propionate, acetone, succinate, ethylene glycol, 1,2-propanediol, phenol and benzoate. No appreciable growth occurs under autotrophic conditions in the presence of $H_2:CO_2$. Fermentation of glycerol yields acetate and 1,3-propanediol as the primary organic products, with significant amounts of $H_2$ produced during growth. Growth is inhibited by ampicillin, chloramphenicol, erythromycin, rifampicin, and kanamycin (all at 100 µg/ml). Streptomycin or tetracycline at the same retards growth. The G+C content of the strain's DNA is 32 mol %, as determined by HPLC.

For the purposes of identifying a putative member of the species *C. viterbiensis*, the term "substantial genomic sequence identity" refers to either: at least 90% identity, preferably at least 95% identity, and more preferably at least 99% identity of the organism's genome sequence with genome sequence of type strain JW/MS-VS5$^T$; or, at least 90% identity, preferably at least 95% identity, and more preferably at least 99% identity of the organism's 16S rDNA sequence with the 16S rDNA sequence of type strain JW/MS-VS5$^T$.

Substantial sequence identity can be determined by the comparison of the entire genomic sequences of a putative *C. viterbiensis* and JW/MS-VS5$^T$. Alternatively, substantial sequence identity can be determined by the comparison of the 16S rDNA sequences of a putative *C. viterbiensis* and JW/MS-VS5$^T$. The sequence of all or a portion of the genome of JW/MS-VS5$^T$ and a putative *C. viterbiensis*, particularly the sequence of the organisms' 16S rDNA, can be determined by conventional nucleic acid sequencing techniques well known to those of skill in the art (see, e.g., Sambrook et al., Molecular Cloning, A Laboratory Manual (1989) and Current Protocols in Molecular Biology (Ausubel et al., eds. 1989)). The sequences can then be compared, using methods of sequence comparison well known to the skilled artisan. For example, percent identity can be calculated using the BLAST computer program, which is described in the art (see, e.g., Altschul et al., *J. Mol. Biol.* 215:403–10 (1990) and Altschul et al., *Nucleic Acids Res.* 25:3389–3402 (1997)).

In a specific embodiment, the invention provides a thermophilic microorganism capable of fermenting glycerol to 1,3-propanediol, the genome of which is hybridizable to the genome of type strain JW/MS-VS5$^T$ under conditions of low stringency. In an alternative preferred embodiment, the invention provides a thermophilic microorganism capable of fermenting glycerol to 1,3-propanediol, the 16S rDNA sequence of which is hybridizable to the 16S rDNA sequence of type strain JW/MS-VS5$^T$ under conditions of low stringency. Procedures using such conditions of low stringency can be as follows (see also Shilo and Weinberg, *Proc. Natl. Acad. Sci. USA* 78:6789–6792 (1981)): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5–20×10⁶ cpm ³²P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which can be used are well known in the art (e.g., as employed for cross-species hybridizations).

In another specific embodiment, the invention provides a thermophilic microorganism capable of fermenting glycerol to 1,3-propanediol, the genome of which is hybridizable to the genome of type strain JW/MS-VS5$^T$ under conditions of moderate stringency. In a preferred embodiment, the invention provides a thermophilic microorganism capable of fermenting glycerol to 1,3-propanediol, the 16S rDNA sequence of which is hybridizable to the 16S rDNA sequence of type strain JW/MS-VS5$^T$ under conditions of moderate stringency. Procedures using such conditions of moderate stringency can be as follows: Filters containing DNA are pretreated for 6 h at 55° C. in a solution containing 6×SSC, 5×Denhart's solution, 0.5% SDS and 100 μg/ml denatured salmon sperm DNA. Hybridizations are carried out in the same solution and 5–20×10⁶ cpm ³²P-labeled probe is used. Filters are incubated in hybridization mixture for 18–20 h at 55° C., and then washed twice for 30 minutes at 60° C. in a solution containing 1×SSC and 0.1% SDS. Filters are blotted dry and exposed for autoradiography. Other conditions of moderate stringency which can be used are well-known in the art. Washing of filters is done at 37° C. for 1 h in a solution containing 2×SSC, 0.1% SDS.

In another specific embodiment, the invention provides a thermophilic microorganism capable of fermenting glycerol to 1,3-propanediol, the genome of which is hybridizable to the genome of type strain JW/MS-VS5$^T$ under conditions of high stringency. In a preferred embodiment, the invention provides a thermophilic microorganism capable of fermenting glycerol to 1,3-propanediol, the 16S rDNA sequence of which is hybridizable to the 16S rDNA sequence of type strain JW/MS-VS5$^T$ under conditions of high stringency. Procedures using such conditions of high stringency can be as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in prehybridization mixture containing 100 μg/ml denatured salmon sperm DNA and 5–20×10⁶ cpm of ³²P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which can be used are well known in the art.

The species *C. viterbiensis* further includes the progeny of the type strain JW/MS-VS5$^T$, including progeny possessing altered genotypes and/or phenotypes relative to type strain JW/MS-VS5$^T$. Phenotypes and/or genotypes can be altered by mutation, including as the result of directed or random mutagenesis. The invention provides cells having single or multiple mutations specifically designed to enhance the production of 1,3-propanediol. For example, it is contemplated that a mutant strain capable of fermenting glycerol to 1,3-propanediol in a manner that is resistant to substrate or product repression would be particularly useful in the present invention.

Methods of creating mutants are common and well known in the art. For example, wild type cells may be exposed to a variety of agents, such as radiation or chemical mutagens, and then screened for the desired phenotype. When creating mutations through radiation, either ultraviolet (UV) or ionizing radiation may be used. Specific methods for creating mutants using radiation or chemical agents are well documented in the art. See, e.g., Brock, *Biotechnology: A Textbook of Industrial Microbiology*, Second Edition (1989) Sinauer Associates, Inc., Sunderland, Mass., or Deshpande, *Appl. Biochem. Biotechnol.*, 36: 227–34 (1992), herein incorporated by reference. Following mutagenic treatement, mutants having the desired phenotype may be selected by a variety of methods. Random screening is most common where the mutagenized cells are selected for the desired attribute. Methods of mutant selection are highly developed and well known in the art of industrial microbiology. See, e.g., Brock, supra.

The instant invention further provides methods for isolating and maintaining in culture thermophilic organisms capable of fermenting glycerol to 1,3-propanediol. Such organisms are useful in practicing embodiments of this invention, e.g., they can be used to biologically convert glycerol to 1,3-propanediol at an elevated temperature, or they can be used as a source of a thermostable enzyme that ferments glycerol, or a polynucleotide encoding the same.

Materials and methods suitable for the maintenance and growth of bacterial cultures can be found, for example, in *Manual of Methods for General Bacteriology* (Gerhardt et al., eds), American Society for Microbiology, Washington, D.C. or Brock, supra. Reagents and materials used for the growth and maintenance of bacterial cells can be obtained from commercial suppliers, for example, Aldrich Chemicals (Milwaukee, Wis.), DIFCO Laboratories (Detroit, Mich.), GIBCO/BRL (Gaithersburg, Md.), or Sigma Chemical Company (St. Louis, Mo.).

A thermophilic organism of the invention, e.g., *C. viterbiensis*, can be isolated from any environment that is conducive to growth of thermophilic organisms, e.g., a thermal vent, hot spring or soil and water and sediments around them, or laundromat effluent. A sample consisting of, for example, sediment, water or a mixture thereof, is collected from the environment of interest. It is desirable to determine the pH and temperature at the sampling point as an indication of optimal conditions for growth of any organism isolated from the sample. The sample is then used innoculate a basal growth medium, preferably a medium wherein glycerol is the sole or primary carbon source. Typically, the basal medium is inoculated with the sample to a final concentration of approximately 10% (w/v). The pH of the medium should preferably approximate that of the sampling point. Alternatively, a plurality of basal growth mediums at different pH can be inoculated to select for organisms having different pH growth dependence. The enrichment culture is then incubated at a high temperature, preferably at least about 50° C., more preferably at least about 60° C., and most preferably at least about 75° C., and is preferably carried out in an anaerobic or microaerobic environment. Guidance for growing thermophilic organisms can be found in, for example, Weigel, J., "Methods for Isolation and Study of Thermophiles", Chapter 4 in *Thermophiles: General, Molecular and Applied Microbiology*, T. D. Brock, ed. (John Wiley & Sons, N.Y.), pp. 17–37.

When an enrichment culture is found to be able to utilize glycerol as a carbon source, a homogeneous culture can be isolated by preparing a dilution series of the culture, plating out the series on a solid basal medium (e.g., 1.5% agar) using soft agar overlays (e.g., basal medium containing 0.8% agar), picking out and subculturing single colonies in liquid medium of the same composition, and checking for the formation of 1,3-propanediol and/or acetate. 1,3-Propanediol can be identified directly by submitting the media to high pressure liquid chromatography (HPLC) analysis. For example, the fermentation media can be analyzed on an analytical ion exchange column using a mobile phase of 0.01 N sulfuric acid in an isocratic fashion. Alternatively, 1,3-propanediol can be identified using other appropriate analytical techniques, including, but not limited to, gas chromatography (GC) and gas chromatography-mass spectroscopy (GC-MS).

A strain of a thermophilic organism found capable of converting glycerol to 1,3-propanediol can be maintained in culture using culture maintenance and preservation techniques known in the art. These methods include refrigeration for short storage times, freezing in liquid nitrogen for prolonged storage, and lyophilization to dehydrate the cells. The choice of the preservation method depends on the nature of the culture and the facilities that are available. When freezing is used, the rates of freezing and thawing must be carefully controlled to ensure the survival of the microorganisms, since ice crystals formed during freezing can disrupt membranes. Glycerol is often employed as an "antifreeze" agent to prevent damage due to ice crystals and to ensure the ability to recover viable microorganisms when frozen cultures are thawed.

Thermostable Enzymes Capable of Producing 1,3-Propanediol at Elevated Temperatures In one embodiment, the instant invention provides a thermostable enzyme that catalyzes a step in the fermentation of glycerol to 1,3-propanediol at elevated temperatures, referred to herein as a "thermostable glycerol fermentation enzyme."

As used herein, the term "thermostable glycerol fermentation enzyme" refers to an enzyme which catalyzes at least one reaction step in the fermentation of a glycerol to 1,3-propanediol and which is "thermostable," i.e., stable and active at high temperatures, preferably at temperatures higher than 50° C., more preferably at temperatures higher than 60° C., still more preferably at temperatures higher than 70° C., and most preferably at temperatures higher than 85° C. An enzyme is "stable" at a given temperature if it is able retain at least 50% of its original catalytic activity after exposure to that temperature for at least 5 minutes, preferably at least 30 minutes, more preferably at least one hour, still more preferably for at least 8 hours, and most preferably for at least 24 hours or longer. In many instances, thermostable enzymes also have increased storage life and are more stable to denaturing conditions, such as physical agitation or exposure to organic solvents, than non-thermostable enzymes sharing similar functional characteristics.

In a preferred embodiment, the invention provides a thermostable glycerol fermentation enzyme that is derived from *C. viterbiensis*. In a preferred, but non-limiting embodiment, the invention provides a thermostable dehydratase derived from *C. viterbiensis*. In another preferred but non-limiting embodiment, the invention provides a thermostable 1,3-propanediol oxidoreductase derived from *C. viterbiensis*. In a particularly preferred embodiment of the invention, the thermostable glycerol fermentation enzyme is derived from strain JW/MS-VS5$^T$.

As used herein, the term "dehydratase" refers to any enzyme that is capable of catalyzing the conversion of a glycerol molecule to the product 3-hydroxypropionaldehyde. Specific examples of dehydratases are glycerol dehydratase and diol dehydratase, i.e., dehydratases having preferred substrates of glycerol and 1,2-propanediol, respectively.

The term "1,3-propanediol oxidoreductase" refers to an enzymes capable of catalyzing the conversion 3-hydroxypropionaldehyde to 1,3-propanediol with the concomitant oxidation of NADH.

The ability to catalyze a reaction step in the fermentation of a glycerol to 1,3-propanediol can be determined by assaying the activity of the enzyme. Glycerol fermentation activity can be assayed using techniques known to those skilled in the art. For example, methods of assaying for the activity of a dehydratase are described by Poppe et al., *Eur. J. of Biochem* 245:398–41 (1997), Honda et al., *J. of Bact.* 143:1458–65 (1980), and Macis et al., *FEMS Microbiology Letters* 164:21–28 (1998), incorporated herein by reference in their entirety. A method of assaying for 1,3-propanediol oxidoreductase activity is described, for example, in Johnson et al., *J. of Bact.* 169:2050–54 (1987), incorporated herein by reference in its entirety. Enzyme activity can be determined in situ using toluene-treated cells, as described for example, by Honda et al. The ability of an enzyme to catalyze a reaction step in the fermentation of a glycerol to 1,3-propanediol can also be determined by expressing the enzyme in a host cell that is not normally capable of fermenting glycerol, and assaying whether expression of the enzyme allows the cell to ferment glycerol.

For the purposes of this invention, a thermostable 1,3-propanediol-producing enzyme is "derived" from *C. viterbiensis*, or a specified strain of *C. viterbiensis*, if: (a) it is endogenously expressed by *C. viterbiensis*, or the specified strain of *C. viterbiensis*, or its amino acid sequence is encoded by a polynucleotide coding sequence that occurs in *C. viterbiensis*, or the specified strain of *C. viterbiensis*; and (b) it is useful in practicing the invention. As used herein, an enzyme is "useful in practicing the invention" if it is a thermostable glycerol fermentation enzyme, i.e., an enzyme that catalyzes at least one reaction step in the fermentation of a glycerol to 1,3-propanediol and which is stable and active at high temperatures, preferably at temperatures higher than 50° C., more preferably at temperatures higher than 60° C., still more preferably at temperatures higher than 70° C., and most preferably at temperatures higher than 85° C.

The invention further provides an enzyme that is homologous to a thermostable glycerol fermentation enzyme derived from *C. viterbiensis*. For the purposes of this invention, an enzyme is "homologous" to a thermostable glycerol fermentation enzyme derived from *C. viterbiensis* if: (a) its amino acid sequence is encoded by a polynucleotide coding sequence that hybridizes to the complement of a polynucleotide sequence that encodes a thermostable glycerol fermentation enzyme derived from *C. viterbiensis* under moderately stringent conditions, i.e., hybridization to filter-bound DNA in 0.5 M NaHPO$_4$, 7% sodium dodecyl sulfate (SDS), 1 mM EDTA at 65° C., and washing in 0.2×SSC/0.1% SDS at 42° C. (Ausubel et al., 1989, Current Protocols in Molecular Biology, Vol. I, Green Publishing Associates, Inc., and John Wiley & sons, Inc., New York, at p. 2.10.3); and (b) it is useful in practicing the invention. In a preferred embodiment, the homologous enzyme is encoded by a polynucleotide coding sequence that hybridizes to the complement of a polynucleotide sequence that encodes a thermostable glycerol fermentation enzyme derived from *C. viterbiensis* under highly stringent conditions, i.e., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel et al., 1989, supra) and is useful in practicing the invention.

An enzyme that is homologous to a thermostable glycerol fermentation enzyme derived from *C. viterbiensis* can take various forms. In some embodiments of the invention, the homologous enzyme is a mutant form of a thermostable glycerol fermentation enzyme derived from *C. viterbiensis*, wherein one or more amino acid residues have been substituted with a different amino acid residue, resulting in an enzyme useful in practicing the invention. Mutations can be conservative, wherein an amino acid residue is substituted with another with another amino acid residue sharing similar functional and structural characteristics, such as acidity, polarity, or bulkiness of side chains. Mutations can also be non-conservative, where the functional and/or structural properties of the substituted amino acid residue are not conserved. In some cases, a mutant form of a thermostable glycerol fermentation enzyme derived from *C. viterbiensis* will possess altered functional properties relative to the native enzymes, such as altered catalytic capability, stability, or pH or temperature optimum. Such mutants fall within the scope of the invention so long as they are homologous to a thermostable glycerol fermentation enzyme derived from *C. viterbiensis*.

Mutant forms of the enzyme can be generated by a variety of techniques well known to the skilled artisan. A number of these techniques are reviewed in U.S. Pat. No. 5,830,696, incorporated herein by reference in its entirety, which describes the directed evolution of thermostable enzymes. Alternatively, mutant enzymes can be created randomly, or occur spontaneously in an organism.

Furthermore, an enzyme that is homologous to a thermostable glycerol fermentation enzyme derived from *C. viterbiensis* can be a deletion mutant or truncated variant of a native *C. viterbiensis* enzyme. The use of such enzyme forms can in some cases be desirable, for example, where a deletion or truncation results in enhanced stability or ease of purification relative to the corresponding native enzyme.

The invention further provides an enzyme that is homologous to a thermostable glycerol fermentation enzyme derived from *C. viterbiensis* that is a chimeric form of a thermostable glycerol fermentation enzyme derived from *C. viterbiensis*, i.e., a protein fusion. Chimeras can be useful, for example, for improving the stability of the enzyme or facilitating purification, e.g., by the inclusion of a moiety capable of associating with an ion exchange, metal chelate, substrate affinity or immunoaffinity matrix. In a preferred embodiment, the invention provides a homologous enzyme covalently attached to a solid support, such as cellulose.

Furthermore, the invention provides an enzyme that is homologous to a thermostable glycerol fermentation enzyme derived from *C. viterbiensis* and that is derived from a different microorganism, preferably a thermophilic microorganism. An example of such an enzyme is a thermostable glycerol fermentation enzyme "homolog," which is defined as an enzyme encoded by a gene from a different species, wherein the gene is recognized by those of skill in the art as a homolog of a *C. viterbiensis* glycerol fermentation gene based on a degree of nucleotide sequence identity greater than about 80%. Sequence identity can be determined using the BLAST program, as described supra.

In one embodiment, the invention provides an isolated thermostable glycerol fermentation enzyme, where the term "isolated" indicates that enzyme is at least partially pure, i.e., provided in a preparation where the percentage by weight of the enzyme, relative to other material in the preparation, is higher than would be found in nature. In a preferred embodiment, the invention provides an isolated thermostable glycerol fermentation enzyme that is at least 90% pure by weight of contaminating proteins, and more preferably at least 95% pure by weight of contaminating proteins.

Materials and methods useful in the preparation and isolation of the aforementioned enzymes are described infra. In one embodiment, an enzyme of the invention can be isolated from a thermophilic organism, particularly a strain of *C. viterbiensis*, that expresses the enzyme endogenously. Alternatively, an enzyme of the invention can be produced recombinantly by introducing a polynucleotide sequence encoding the enzyme into an appropriate host cell and expressing the encoded gene product. An enzyme of the invention can also be produced by means of in vitro translation, or by chemical synthesis techniques.

Methods of Cloning a Polynucleotide Encoding a Thermostable Enzyme that Converts Glycerol to 1,3-Propanediol The instant invention provides a polynucleotide sequences encoding a thermostable glycerol fermentation enzyme, or a fragment thereof, and methods for identifying, isolating, and cloning such polynucleotides. These methods involve providing a sample containing polynucleotide coding sequences derived from a thermophilic organism or thermophilic organisms, and screening for a polynculeotide sequence encoding a thermostable glycerol fermentation enzyme, or a fragment thereof. The sample can take any of a variety of forms, and be prepared by a variety of different techniques known to those of skill in the art. Similarly, screening of the sample can be accomplished using any of a number of suitable techniques, some non-limiting examples of which are described infra.

Production and manipulation of the polynucleotide molecules and oligonucleotide molecules disclosed herein are within the skill in the art and can be carried out according to recombinant techniques described, among other places, in Sambrook et al., Molecular Cloning, a Laboratory Manual (1989); Current Protocols in Molecular Biology (Ausubel et al. eds., 1989); PCR Strategies (Innis et al. eds., 1995);and PCR Technology (Erlich ed., 1992), all of which are incorporated herein by reference.

In some embodiments of the invention, the sample is screened with a probe having a nucleotide sequence believed to encode a glycerol fermentation enzyme, or a probe or probes representing a portion thereof. A probe sequence can be based on the amino acid sequence of a known glycerol fermentation enzyme, or some fragment thereof, or a polynucleotide sequence encoding such an enzyme. For example, the amino acid sequence of a portion of a glycerol-fermentation enzyme can be determined, using amino acid sequencing techniques described, e.g., in Creighton, Protein Structures and Molecular Principles (1983), and the information used to generate a set of degenerate probes. In a preferred embodiment of the invention, a sample is screened using a probe or probes based upon a sequence encoding a dehydratase or oxidoreductase derived from a thermophilic organism such as *C. viterbiensis*. Alternatively, the probe can be based upon a glycerol fermentation enzyme-encoding gene derived from a non-thermophilic organism (e.g., *K. pasteurianum*, *C. freundii*, or *C. pasteurianum*), such as the dhaBCE or dhaT genes, which encode glycerol dehydratase and oxidoreductase, respectively. The nucleotide sequences of dhaBCE genes have been reported in the literature (see, e.g., Macis et al., *FEMS Mocrobiology Letters* 164:21–28 (1998) (*C. Pasteurianum*); Seyfried et al., *J. of Bacteriology* 178:5793–96 (1996) (*C. freundii*); and Tobimatsu et al., *J. Biol. Chem.* 271:22352–57 (1996) (*K. pneumoniae*)). The nucleotide sequences of dhaT gene have also been reported (see, e.g., Luers et al., *FEMS Microbiol. Lett.* 154:337–45 (1997) (*C. Pasteurianum*); and Daniel et al., *J. of Bacteriol.* 177:2151–56 (1995) (*C. freundii*)). Specific probes provided by this invention include primer pairs based on the dhaB gene of *K. pasteurianum* (e.g., as detailed below by way of illustrative embodiments in dhaB15' (SEQ ID NO:1); dhaB13' (SEQ ID NO:2); dhaB25' (SEQ ID NO:3); dhaB23' (SEQ ID NO:4); dhaB35' (SEQ ID NO:5); and dhaB33' (SEQ ID NO:6)) which are particularly useful for amplifying a glycerol fermentation enzyme-encoding polynucleotide, or a fragment thereof, via polymerase chain reaction ("PCR"). Such a primer pair can be used to amplify a segment of a glycerol fermentation enzyme-encoding polynucleotide from an organism of interest, which can in turn be used as a probe for identifying and cloning the full-length coding sequence from the same or a different organism. Probes can be labeled for identifying homologous sequences, for example in a cDNA library. Alternatively, probes can be used as primers to amplify a polynucleotide sequence flanked by sequences recognized by the primers, particularly by means of PCR or RT-PCR. In particular, a sequence of interest can be amplified from a cDNA or genomic library, from an isolated organism, or from an environmental sample, as described in more detail below.

In one embodiment of the invention, the sample to be screened is an environmental sample suspected of harboring a thermophilic organism, such as a water, soil or mud sample collected from an environment conducive to thermophilic life. Typically, an environmental sample will be prepared in a manner such that nucleic acids present in the sample are available for interaction with a complementary probe, e.g., a PCR primer. A glycerol fermentation enzyme-encoding polynucleotide, or a fragment thereof, can be recognized by its ability to hybridize to a probe as described above.

A preferred method of isolating and cloning a polynucleotide of the invention from an environmental sample is by means of PCR. This technique takes advantage of the sequence homology between polynucleotides encoding homologous enzymes, or enzymes with similar activity. The method employs a set of primers based on a known glycerol fermentation enzyme-encoding polynucleotide sequence, or a portion thereof, to amplify a homologous polynucleotide sequence, or a fragment thereof, from an environmental sample. The homologous polynucleotide can be amplified from DNA in the sample, particularly genomic DNA of microorganims in the sample, using conventional PCR methodology well known in the art. Alternatively, the homologous polynucleotide can be amplified from RNA in the sample, particularly mRNA or total RNA, by synthesizing a first-strand cDNA copy of RNA and amplifying the cDNA via PCR, e.g., RT-PCR. Using techniques known to those of skill in the art, one can adjust the annealing conditions of the reaction to allow hybridization of primers at a desired level of homology, thereby permitting the amplification of sequences sharing more or less homology with the sequence upon which the primers are based. This method allows for the isolation of a complete glycerol fermentation enzyme-encoding open reading frame ("ORF"), or a fragment thereof. One or more fragments of a glycerol fermentation enzyme-encoding ORF can be cloned and spliced together so as to produce a complete ORF. The amplified glycerol fermentation enzyme-encoding ORF can then be used to express the encoded glycerol fermentation enzyme in the practice of various aspects of the invention. For example, the sequence can be introduced into a host cell, thereby enabling the host cell to ferment glycerol. Alternatively, the expressed enzyme can be purified for applications such as cell-free fermentation. Alternatively, the ORF sequence can itself be used to design novel primers and probes for the further detection and isolation of novel thermostable glycerol fermentation enzyme-encoding sequences.

In another embodiment of the invention, the sample is a polynucleotide library, preferably a genomic or cDNA library prepared from a thermophilic organism, especially an organism known to be capable of fermenting glycerol to 1,3-propanediol. For general background on molecular biology techniques and on how to prepare a cDNA library and a genomic library, see, e.g., Ausubel et al., supra; Sambrook et al., supra; and U.S. Pat. No. 5,650,148. The library can be screened using nucleic acid hybridization screening techniques in conjunction with the appropriate labeled probes, as described above. Appropriate screening techniques are set forth, among other places, in Benton and Davis, *Science* 196:180 (1977) (bacteriophage libraries) and Grunstein and Hogness, *Proc. Natl. Acad. Sci. USA* 72:3961–65 (1975) (plasmid libraries), which publications are incorporated herein by reference.

In still another embodiment of the invention, the sample comprises an isolated organism or organisms, or a polynucleotide library generated from an isolated organism or organisms, from which a polynucleotide of the invention can be amplified using PCR or RT-PCR. Preferably, the isolated organism or organisms used are thermophilic and capable of fermenting glycerol.

In one embodiment of the invention, an expression library is constructed which is able to direct the expression of the gene products encoded by the polynucleotide constituents of the library.

In a particularly preferred embodiment of the invention, an expression library is functionally screened by testing its constituents for the ability to encode a gene product that catalyzes a step in the fermentation of glycerol. In a preferred embodiment, an organism that is normally incapable of fermenting glycerol to 1,3-propanediol is tranformed with a constituent of a DNA library as described above, preferably a library prepared from a thermophilic organism known to be capable of fermenting glycerol. The transformed organisms are then screened for the ability to ferment glycerol to 1,3-propanediol by their anaerobic growth on glycerol. The transformed microorganisms can be screened for the production of 1,3-propanediol and/or acetate. The ability to grow anaerobically on glycerol, or to produce 1,3-propanediol and/or acetate, indicates that the library constituent used to transform the organism encodes an enzyme that is able to provide an enzymatic activity required for the fermentation of glycerol. The library constituent can then be cloned and characterized by standard techniques and used in the practice of various aspects of the instant invention.

The microorganism transformed in the functional cloning strategy described above can be one that inherently lacks the ability to ferment glycerol, or a microorganism that has lost the ability to ferment glycerol as the result of a mutation, e.g., a null mutation in one of the genes required for glycerol fermentation. Such a mutation can be engineered into an organism using techniques well known in the art. The microorganism can, but need not necessarily be, thermophilic. It is preferable that the test organism possess all but one of the enzymatic activities required for glycerol fermentation, so that the ability to ferment glycerol can be recovered by the introduction of a single enzymatic activity.

Alternatively, the expressed gene products can be immunologically screened using standard techniques in conjunction with antibodies raised against a glycerol fermentation enzyme. For such screening techniques, see, e.g., Antibodies: A Laboratory Manual (Harlow and Lane, eds., 1988).

Recombinant Organisms Capable of Fermenting Glycerol to 1,3-Propanediol

The instant invention also provides a recombinant organism that has been genetically engineered to express one or more exogenous, i. e., heterologous, thermostable glycerol fermentation enzymes. The term "exogenous," when used in this context, indicates that enzyme is encoded by an heterologous polynucleotide coding sequence, i.e., a polynucleotide sequence that is not native, or endogenous, to the host organism. In a preferred embodiment, the recombinant organism is engineered to express a thermostable glycerol fermentation enzyme derived from *C. viterbiensis,* or an enzyme that is homologous to such an enzyme. In a particularly preferred embodiment, the recombinant organism is engineered to express a dehydratase or 1,3-propanediol oxidoreductase derived from a strain of *C. viterbiensis,* such as JW/MS-VS5$^T$.

A recombinant organism of the invention can be useful in the practice of various aspects of the instant invention. For example, the recombinant organism can be used as a catalyst in a process for biologically converting glycerol to 1,3-propanediol. In another non-limiting embodiment, the recombinant organism can serve as the source of a thermostable glycerol fermentation enzyme, which can be isolated using protein purification techniques familiar to the skilled artisan.

The invention provides a variety of vectors and transformation and expression cassettes suitable for cloning, transformation and expression of a polynucleotide sequence encoding a thermostable glycerol fermentation enzyme, or a fragment thereof. Suitable vectors will be those which are compatible with the host microorganism and the intended use of the resulting recombinant microorganism. For example, a suitable vector can be derived from a plasmid, a virus (such as bacteriophage T7 or a M13 derived phage), or a cosmid. Protocols for obtaining and using such vectors are known to those in the art. See, e.g., Sambrook et al., supra.

Typically, the vector or cassette contains sequences directing transcription and translation of the relevant gene, a selectable marker, and sequences allowing autonomous replication or chromosomal integration. Suitable vectors comprise a region 5' of the coding sequence that harbors transcriptional initiation controls and a region 3' of the coding sequence that controls transcriptional termination. In a preferred embodiment, control regions are derived from genes homologous to the transformed host cell.

Recombinant vectors of the present invention, particularly expression vectors, are preferably constructed so that the coding sequence is in operative association with one or more regulatory elements necessary for transcription and translation of the coding sequence. As used herein, the term "regulatory element" includes but is not limited to nucleotide sequences that encode inducible and noninducible promoters, enhancers, operators and other elements known in the art to drive and/or regulate expression of polynucleotide coding sequences. Also, as used herein, the coding sequence is in "operative association" with one or more regulatory elements where the regulatory elements effectively regulate or allow for the transcription of the coding sequence or the translation of its mRNA, or both.

The regulatory elements of these vectors can vary in their strength and specificities. Depending on the host/vector system utilized, any of a number of suitable transcription and translation elements can be used. Non-limiting examples of transcriptional regulatory regions or promoters for bacteria include the β-gal promoter, the T7 promoter, the TAC promoter, lambda left and right promoters, trp and lac promoters, and the trp-lac fusion promoters.

General methods of expressing recombinant proteins are well known in the art, as exemplified in R. Kaufman, *Methods in Enzymology* 185:537–566 (1990). Optionally, the heterologous sequence can encode a fusion protein including an N-terminal identification peptide imparting desired characteristics, e.g., stabilization or simplified purification of expressed recombinant product.

To direct the glycerol fermentation enzyme into the secretory pathway of the host cells, a secretory signal sequence may be provided in the expression vector. The secretory signal sequence is joined to the polynucleotide sequence encoding the glycerol fermentation enzyme in the correct reading frame. Secretory signal sequences are commonly positioned 5' to the coding sequence. The secretory signal sequence may be that normally associated with a protein secreted by the host organism.

Once a suitable transformation or expression vector has been constructed, it can be used to transform an appropriate host cell, using known procedures such as, e.g., calcium-permeabilized cells, electroporation, protoplast transformation, or by transfection using a recombinant phage virus. Suitable expression hosts include *E. coli, Bacillus subtilis, Salmonella typhimurium* and various species within the genera Bacillus, Pseudomonas, Streptomyces, and Staphylococcus, although others may also be employed as a matter of choice.

In a preferred embodiment, the invention provides a thermophilic recombinant microorganism that has been genetically engineered to express one or more exogenous thermostable glycerol fermentation enzymes. Such microorganims are particularly useful in the biological conversion of glycerol to 1,3-propanediol, as described infra. Examples of thermophilic microorganisms include members of the genera Bacillus, Thermus, Sulfolobus, Thermoanaerobacter, Thermobrachium, and Caloramator.

The selected host microorganism will preferably be able to produce the co-factor adenosyl-cobalamin (coenzyme $B_{12}$). If necessary, $B_{12}$ synthesis genes can be introduced the microorganism and/or the media can be supplemented with vitamin $B_{12}$.

Methods for Isolating Thermostable Glycerol Fermentation Enzymes

The instant invention provides a method for preparing and isolating a thermostable glycerol fermentation enzyme. In a preferred embodiment, the enzyme is provided in a substantially purified form. In a non-limiting embodiment, the enzyme is isolated from a thermophilic microorganism that expresses a native thermostable glycerol fermentation enzyme. In another non-limiting embodiment, the enzyme is isolated from a recombinant organism engineered to express an exogenous polynucleotide sequence encoding a thermostable glycerol fermentation enzyme. Alternatively, a thermostable enzyme of the invention can be prepared using conventional solution or solid phase peptide syntheses procedures, as described in, e.g., Creighton, supra.

Host cells expressing the thermostable glycerol fermentation enzyme of interest are typically cultivated in a nutrient medium suitable for production of the enzyme, using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the enzyme to be expressed and/or isolated. A suitable nutrient medium typically comprises carbon and nitrogen sources and inorganic salts, using procedures known in the art. Suitable media are available from commercial suppliers, or may be prepared according to published compositions (e.g., in catalogs of the American Type Culture Collection).

Depending on the nature of the host cell and expression vector used, the enzyme may be retained in the cytoplasm, often as insoluble granules (known as inclusion bodies), or may be directed to the periplasmic space by a bacterial secretion sequence. In the former case, the cells are lysed and the granules are recovered and denatured, after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme. If the enzyme is secreted into the nutrient medium, it can be recovered directly from the medium.

Enzyme produced by the cells may then be recovered by means of conventional techniques known in the art, including, but not limited to, centrifugation, filtration, extraction, spray-drying, evaporation, differential solubility (e.g., ammonium sulfate precipitation), chromatography (e.g., ion exchange, affinity, hydrophobic, chromatofocusing, and size exclusion) or electrophoretic procedures (e.g., preparative isoelectric focusing (IEF) (see, e.g., Protein Purification (Janson and Ryden eds., 1989); Scopes, Protein Purification: Principles and Practice (1994); Sambrook et al. supra; and Ausubel et al. supra.

In a preferred embodiment, the enzyme is purified as a fusion protein including a fusion element that facilitates rapid affinity purification. Useful purification fusion elements include histidine and glutathione S-transferase (GST) tags. A protease recognition site, e.g., a thrombin or factor Xa recognition site, can be included to permit cleavage of the desired protein product from the fusion element. Vectors useful for the construction of gene fusion expression systems are commercially available, for example from Amersham Pharmacia Biotech, Inc. (Piscataway, N.J.).

Specific protein purification protocols useful for isolating glycerol fermentation enzymes have been described in the literature (see, e.g., Seyfried et al., *J. of Bact.* 178:5793–96 (1996) (glycerol dehydratase); Tobimatsu et al., *J. of Bact.* 181:4110–13 (1996) (glycerol dehydratase); and Johnson et al., *J. of Bact.* 169:2050–54 (1987) (1,3-propanediol oxidoreductase). For example, Seyfried et al. describe the use of a vitamin $B_{12}$-agarose resin as an affinity matrix for the purification of glycerol dehydratase.

Methods of Biologically Converting Glycerol to 1,3-Propanediol

The present invention provides biological methods for converting glycerol to 1,3-propanediol. As used herein, a "biological" method of converting glycerol to 1,3-propanediol is a method that employs a biological catalyst, e.g., a glycerol fermentation enzyme, either as a constituent of a microorganism or in a cell-free enzyme catalyzed reaction system. In particular, the invention provides biological conversion processes that can be carried out at high temperatures, catalyzed by a thermophilic organism and/or thermostable enzyme. In a preferred embodiment, the method is carried out at temperatures higher than 50° C., more preferably at temperatures higher than 60° C., and employs a thermophilic microorganism capable of fermenting glycerol to 1,3-propanediol.

In a non-limiting embodiment, the process employs a thermophilic microorganism that naturally expresses a full complement of thermostable glycerol fermentation enzymes, sufficient to catalyze all reaction steps in the fermentation of glycerol to 1,3-propanediol, e.g., 1,3-propanediol oxidoreductase, glycerol dehydratase and/or diol dehydratase. In a particularly preferred embodiment, a strain of *C. viterbiensis,* e.g., strain JW/MS-VS5$^T$, is employed as the biological catalyst.

In an alternative embodiment, the process employs a recombinant microorganism, preferably a thermophilic recombinant microorganism, that has been genetically engineered to express one or more exogenous thermostable glycerol fermentation enzymes. Examples of thermophilic microorganisms include members of the genera Bacillus, Thermus, Sulfolobus, Thermoanaerobacter, Thermobrachium, and Caloramator. The term "exogenous," when used in this context, indicates that enzyme is encoded by an heterologous polynucleotide coding sequence, i.e., a polynucleotide sequence that is not native, or endogenous, to the thermophilic host organism. In a preferred embodiment, the heterologous polynucleotide sequence encodes a thermostable glycerol fermentation enzyme derived from *C. viterbiensis,* or an enzyme that is homologous to such an enzyme. In a particularly preferred embodiment, the heterologous polynucleotide sequence is derived from a strain of *C. viterbiensis.*

Optionally, a thermophilic microorganism used in the process of the invention can produce the co-factor adenosylcobalamin (coenzyme $B_{12}$). If necessary, $B_{12}$ synthesis genes can be introduced the microorganism and/or the media can be supplemented with vitamin $B_{12}$.

The invention provides a fermentation process for the bioconversion of glycerol to 1,3-propanediol using a thermophilic organism of the invention. The fermentation conditions should be optimized, balancing cost and convenience with product yield and efficiency. The development of a commercial fermentation process typically occurs in a stepwise fashion, initially using small flasks, then small fermentors (under 10 gallons), intermediate size fermentors (up to several hundred gallons), and finally, large scale fermentors (thousands of gallons). At each stage of production, development conditions are adjusted to produce maximal yields at minimal costs. The organic and inorganic composition of the medium, as well as the pH, temperature, and oxygen concentration, are the main factors that are varied to maximize the efficiency of the production process. Even in a batch process, conditions are often varied during fermentation to achieve the maximal product yield, and conditions are monitored during the fermentation process to ensure that critical parameters remain within the allowable limits. The reaction chambers and substrate solutions should be sterilized prior to the addition of the microbial strain being used in the production process. When fermenting at lower temperature, infection of the reaction with microbial contaminants can easily lead to a competitive displacement of the strain being employed to produce the product, with obviously deleterious results. An important advantage of the present invention is that by using thermophilic organisms and/or thermostable enzymes, the reaction can be run at high temperatures where most potential contaminants are not viable.

The composition of the fermentation medium must include the nutrients essential to support the growth of the microorganism and formation of the desired product. Essential nutrients include sources of carbon, nitrogen and phosphorous. The choice of a particular nutritive source is made on economic as well as biological grounds. Depending on the nature of the fermentation process, all of the raw ingredients may be added at the beginning of the fermentation, or nutrients may be fed to the microorganisms gradually throughout the process.

The pH of the reaction can substantially affect fermentation. The enzymes involved in forming the desired product all have optimal pH ranges for maximal activity and limited pH ranges in which activity is maintained. The rapid growth of organisms in a fermentor can quickly alter the pH of the reaction medium. For example, the accumulation of acid, e.g., acetic acid, can cause the pH of a nonbuffered medium to decline precipitously, inhibiting or halting production of the desired fermentation product. To prevent such changes, the fermentation medium should be buffered to dampen pH changes. Additionally, the pH of the reaction solution normally is continuously monitored, and acid or base is added as need to maintain it within acceptable tolerance limits. In fermentation processes employing strain JW/MS-VS5$^T$, the pH of the medium should be maintained between about 5.0 to 7.8, preferably between about pH 6.0 and 6.5.

The temperature of the reaction should also be carefully regulated to achieve optimal yield of product. Heating coils can be used to maintain elevated temperatures so as to achieve optimal rates of product formation and to inhibit infection by microbial contaminants. The heating coils can also be used for periodic sterilization of the fermentor chamber. Fermentation can be carried out at any temperature consistent with activity and viability of the microorganism. In a preferred embodiment the invention is carried out at a temperature of at least 40° C., preferably at a temperature of at least 50° C., and most preferably at a temperature of 60° C. or greater. In fermenation processes employing strain JW/MS-VS5$^T$, the temperature should be maintained between 33 and 64° C., preferably between 50 and 64° C., and most preferably between 57 and 64° C.

In addition to its nutritional and environmental parameters, a fermentation process may be designed as a batch process, which is analogous to inoculating a flask containing a broth with a microbial culture, or as a continuous flow process, which is analogous to that of a chemostat. The choice of the process design depends on the economics of both production and recovery of the desired product. Compared to batch processes, flow-through fermentors are more prone to contamination with undesired organisms, which can make quality control difficult to maintain, particularly if the fermentation is conducted at a moderate temperature. The flow-through design, however, has the advantage of producing a continuous supply of product that can be recovered at a constant rate for commercial distribution. By their very nature, batch processes require significant startup time to initiate the fermentation process, incubation times to allow fermentation products to accumulate, and recovery times during which the product is separated from the spent medium and microbial cells.

In another embodiment of the invention, the process can be used to convert a fermentable carbon substrate other than glycerol to 1,3-propanediol. In a non-limiting embodiment, a thermophilic microorganism capable of converting a fermentable carbon substrate, for example, a monosaccharide such as glucose or a polysaccharide, to glycerol can be engineered to produce 1,3-propanediol by recombinantly introducing into the microorganism the complement of thermostable 1,3-propanediol producing enzymes necessary for converting glycerol into 1,3-propanediol. These enzymes can be derived from a thermophilic organism capable of converting glycerol to 1,3-propanediol, for example *C. viterbiensis*. Techniques for recombinantly engineering the enzymatic activity required to ferment glycerol into 1,3-propanediol into a non-thermophilic organism are described in U.S. Pat. No. 5,686,276, incorporated herein by reference in its entirety.

Alternatively, a recombinant microorganism of the invention can be engineered to ferment carbon sources other than glycerol to 1,3-propanediol. The use of such organisms can be advantageous, particularly for the production of 1,3-propanediol from inexpensive carbon sources such as glucose or fermentable polysaccharides. For example, a microorganism capable of fermenting glycerol to 1,3-propanediol can be engineered to convert a glycolytic intermediate, e.g., dihydroxyacetone phosphate, into glycerol, thereby permitting the introduction of carbon from non-glycerol sources into the fermentation pathway. WO 98/21340, incorporated herein by reference in its entirety, describes methods for the production of glycerol from a recombinant organism by transforming a suitable host cell with an expression cassette comprising either or both a gene encoding a glycerol-3-phosphate dehydrogenase enzyme and a gene encoding a glycerol-3-phosphate phosphatase enzyme. Such organisms are able to ferment simple sugars, e.g., glucose, into glycerol. These organisms, or indeed any organism genetically engineered to produce these enzymes or alternative glycerol synthetic pathway enzymes, can be used as host cells for the further fermentation of glycerol to 1,3-propanediol using the compositions and methods of the invention. Further, WO 98/21339, incorporated herein by reference in its entirety, describes recombinant microorganisms engineered to express genes encoding glycerol-3-phosphate dehydrogenase, glycerol-3-phosphatase, glycerol dehydratase and 1,3-propanediol oxidoreductases, and thereby enabled to convert glucose and other sugars to 1,3-propanediol. Thus, this strategy can be applied by one skilled in the art to produce 1,3-propanediol from any carbon substrate that can be converted to either glycerol, dihydroxyacetone, $C_3$ compounds at the oxidation state of glycerol (e.g., glycerol 3-phosphate), or $C_3$ compounds at the oxidation state of dihydroxyacetone (e.g., dihydroxyacetone phosphate or glyceraldehyde 3-phosphate) (see, e.g., WO 98/21339).

In another embodiment of the invention, the recombinant thermophilic organism used can be engineered to express, or express at enhanced levels, a protein capable of suppressing the inactivation of a glycerol fermentation enzyme. For example, techniques described in WO 98/21341, incorporated herein by reference in its entirety, can be used to introduce the expression of an enzyme capable of reversing the substrate-mediated inactivation of glycerol dehydratase.

The process of the invention is carried out in a medium that contains the carbon substrate to be converted into 1,3-propanediol, preferably as the sole or primary carbon source. In a preferred embodiment, a basal medium is used wherein glycerol is present as the sole or primary carbon source. In addition to an appropriate carbon source, fermentation media must contain suitable minerals, salts, cofactors, buffers and other components, known to those skilled in the art, suitable for the growth of the cultures and promotion of the enzymatic activities necessary for the production of 1,3-propanediol. Particular attention should be given to Co(II) salts and/or vitamin $B_{12}$ or precursors thereof. A specific non-limiting example of a suitable medium for use in the conversion of glycerol to 1,3-propanediol by *C. viterbiensis* is provided below in the Examples.

The process of the invention can be carried out under aerobic or anaerobic conditions, where anaerobic or microaerobic conditions are preferred. In a particularly preferred embodiment the process is carried out under a nitrogen or argon atmosphere, for example, under an atmosphere of $N_2/CO_2$ at ratio of 80:20. Chemicals may also be added that react with and remove molecular oxygen from the growth medium. For example, sodium thioglycollate will react with free oxygen and remove it from solution. Similarly, the amino acid cysteine and other compounds containing sulfhydryl groups can also be used to scavenge molecular oxygen from a growth medium. For liquid cultures, nitrogen may be bubbled through the medium to remove air and traces of oxygen, after which the culture vessel is tightly sealed to prevent oxygen from reentering.

Additionally, an anaerobic culture chamber may be employed to exclude oxygen from the atmosphere. Common forms of anaerobic chambers, such as the Gas Pak system, generate hydrogen, which reacts with the oxygen as a catalyst within the chamber to produce water. Carbon dioxide is also generated in this system to replace the volume of gas depleted by the conversion of oxygen to Water.

1,3-Propanediol may be identified directly by submitting the media to high pressure liquid chromatography (HPLC) analysis. For example, fermentation media can be analyzed on an analytical ion exchange column using a mobile phase of 0.01 N sulfuric acid in an isocratic fashion. Alternatively, 1,3-propanediol can be identified using other appropriate analytical techniques, including, but not limited to, gas chromatography (GC) and gas chromatography-mass spectroscopy (GC-MS).

1,3-propanediol from can be purified from the fermentation media using techniques known to the skilled artisan, including distillation, centrifugation, filtration and chromatographic separation. For example, propanediols can be obtained from cell media by subjecting the reaction mixture to extraction with an organic solvent, distillation and column chromatography, as described, for example, in U.S. Pat. No. 5,356,812, incorporated herein by reference in its entirety. A particularly good organic solvent for this process is cyclohexane, as described in U.S. Pat. No. 5,008,473.

Alternatively, 1,3-propanediol can be produced in a fermentation system employing enzymes and/or microbial cells adsorbed or bonded to a solid support, such as cellulose. The bonded and thus immobilized enzymes act as a solid-surface catalyst. A solution containing the reaction substrate, e.g., glycerol, is then passed across the solid surface. Temperature, pH and oxygen concentration are set at optimal levels to achieve maximal rates of conversion. This type of process is particularly appropriate when the desired transformation involves a single metabolic step, e.g., the conversion of glycerol to an intermediate in the formation of 1,3-propanediol, or the conversion of such an intermediate to 1,3-propanediol. The process is more complex when multiple enzymatic activities are required to convert an initial substrate into a desired product. Generally the process medium must include any ancillary factors required for catalysis, such as enzyme cofactors (e.g., vitamin $B_{12}$) and reducing equivalents. The desired product can be purified from the fermentation media using the techniques described supra. When using such immobilized systems, it is essential to provide conditions that maintain enzymatic activity and minimize the inactivation or loss of enzyme. When whole cells, rather than cell-free enzymes, are employed in such immobilized systems, it is important to maintain viability of the microorganisms during the process. This process using immobilized cells generally involves adding necessary growth substrates.

The process according to the invention enables glycerol to be converted substantially stoichiometrically into 1,3-propanediol. The yield of 1,3-propanediol is often of the order of 2 moles of 1,3-propanediol from 3 moles of glycerol. In the present context, substantially is understood to mean glycerol consumption of at least 80%, and preferably at least 95%.

The 1,3-propanediol produced by the methods and compositions of the invention is useful in the production of polyesters and films. For example, poly(1,3-propylene terephthalate) (PPT) has been synthesized by Whinfield and Dickson using 1,3-propandiol as the starting material. The physical properties of PPT are superior than those of the generally commercially available polyester poly(ethylene terephthalate) (PET). Other processes for synthesizing PPT are described in, for example, U.S. Pat. Nos. 5,340,909 and 5,872,204, incorporated by reference herein. Other polymers can also be synthesized.

The following examples are provided to illustrate, but not limit, the instant invention.

EXAMPLE

Isolation of *C. viterbiensis* Type Strain JW/MS-VS5$^T$

Materials and Methods

Source of organism

The strain was isolated from a mixed sediment/water sample collected from a freshwater hot spring in the Bagnaccio Spring area near Viterbo, Italy, in June 1997. Temperatures at sampling points were 63° C. and the pH was 6.6–6.7. Conditions are described more fully in Canganella et al., *J. Basic Microbiol.* 35:9–19 (1995), incorporated by reference herein in its entirety.

Media and cultivation

A basal medium used for enrichment, isolation and cultivation was prepared by the modified Hungate technique under $N_2/CO_2$ (80:20) gas phase, as described in Ljungdahl et al., Manual of Industrial Microbiology and Biotechnology (Demain and Solomon eds., 1896). The basal medium contained (per liter of deionized water): 0.5 g $(NH_4)_2SO_4$, 0.5 g $NH_4Cl$, 2.0 g $KH_2PO_4$, 0.04 g $MgCl_2*6H_2O$, 0.04 g $CaCl_2*2H_2O$, 4.2 g $NaHCO_3$, 0.13 g $Na_2S*9H_2O$, 0.13 g cystein-HCl, 0.3 g yeast extract, 0.001 g resazurin, 3.0 g glycerol, 2 ml vitamins solution (described in Wolin et al., *J. Biol. Chem.* 238:2882–86 (1963)) and 1 ml trace elements solution. The trace elements solution contained (mmol/l): 2.0 $(NH_4)_2Fe(SO_4)_2*6H_2O$, 1.0 $CoCl_2*6H_2O$, 1.0 $(NH_4)_2Ni(SO_4)_2*6H_2O$, 0.1 $Na_2MoO_4*2H_2O$, 0.1 $Na_2WO_4*2H_2O$, 0.5 $ZnSO_4*7H_2O$, 0.01 $CuCl_2*2H_2O$, 0.5 $Na_2SeO_3$, 0.1 $H_3BO_3$, 0.5 $MnCl_2*4H_2O$, and 0.01 $AlK(SO_4)_2*12H_2O$. The pH was adjusted to 6.0 (at 25° C.). Enrichments and pure cultures were grown usually in 10 ml medium in Hungate tubes under an atmosphere of $N_2/CO_2$ (80:20). All incubations were at 60° C. unless noted otherwise.

Determination of growth

Growth of bacteria was determined by measuring the increase in optical density at a wavelength of 600 nm (Spectronic 21, Bausch & Lomb, Rochester, N.Y.).

pH and temperature ranges

For the determination of the pH range for growth, the pH was determined at 25° C. using a model 815 MP pH meter (Fisher Scientific, Pittsburg, Pa.). Temperature range for growth was determined using a temperature gradient incubator (Scientific Industries, Inc., Bohemia, N.Y.) under shaking (15 spm) in basal medium at $pH^{25C}$ 6.0.

Substrate utilization

The ability of the organism to utilize different substrates was tested using the basal medium supplemented with autoclaved or filter-sterilized substrates instead of glycerol.

The cultures were incubated for two weeks and monitored for growth by measuring optical density.

Electron acceptors

The potential use of different electron acceptors was studied in the basal medium containing glycerol (3 g/l) as substrate. The different electron acceptors were added from autoclaved stock solutions. Cultures grown in basal medium were used as an inoculum (10% v/v). The use of the electron acceptors (10 mM) was monitored by determination of nitrite production (for nitrate), sulfide production (for sulfate and elemental sulfur) or change in color (AQDS).

Antibiotic susceptibility

Susceptibility to antibiotics was determined by transferring an exponentially growing culture into fresh basal media containing 100 g/ml of filter-sterilized antibiotics. The cultures were incubated for two weeks.

Microscopy

Routine examinations were performed using light microscopy (model PM 10AD, Olympus Optical Co., Ltd, Tokyo, Japan, equipped with phase-contrast optics). Transmission electron microscopy was performed with a model 100CX electron microscope (JEOL, Tokyo, Japan). The samples used for ultrathin sectioning were prepared by using uranyl acetate and lead citrate for poststaining as described by Spurr, *J. Ultrastruc. Res.* 26:31–43 (1969). Gram staining was performed by the method of Hucker (Doetsch in Manual of Methods for General Microbiology (Gerhardt et al., eds. 1981)).

Analytical techniques

Determination of glycerol, glucose, short-chain organic acids and alcohols was performed by high-performance liquid chromatography (HPLC) as previously described in Svetlitshnyi et al., *Int. J. Syst. Microbiol.* 46:1131–37 (1996). Molecular hydrogen was analyzed by gas chromatography (Svetlitshnyi et al.). Production of nitrite was measured using an enzymatic analysis kit from Boehringer Mannheim (catalog no. 905608). Sulfide was determined by the method of Cord-Ruwisch, *J. Microbiol. Methods.* 4:33–36 (1985).

G+C content of DNA

The DNA was isolated and purified using the QIAGEN Genomic DNA purification protocol according to the manufacturer's instructions. The DNA was digested enzymatically, and the guanine-plus-cytosine (G+C) content was determined by separating the nucleosides by HPLC as described by Whitman et al., *Syst. Appl. Microbiol.* 7:235–240 (1986) and Mesbah et al., *Int. J. Syst. Bacteriol.* 39:159–167 (1989).

16S rRNA gene sequence determination and phylogenetic analyses

The extraction of genomic DNA, PCR amplification of the 16S rRNA gene and sequencing of the purified PCR products were carried out as described in Rainey et al., *Int. J. Syst. Bacteriol.* 46:28–96 (1996). Sequence reaction products were purified by ethanol precipitation and electrophoresed with a model 310 Genetic Analyzer (Applied Biosystems, Foster City, Calif.). The 16S rRNA gene sequences obtained in this study were aligned against the previously determined low G+C Gram positive sequences available from the public databases using the ae2 editor Maidak et al., *Nucleic Acids Res* 27:171–173 (1999). The programs of the PHYLIP package including DNADIST and NEIGHBOR were used for the phylogenetic analyses (Felsenstein (1993), phylogenetic inference package, version 3.5.1. Department of Genetics, University of Washington, Seattle). The method of Jukes et al. in Mammalian Protein Metabolism (Munro, ed., 1969), was used to calculate evolutionary distances. The tree topology was reanalyzed using 1000 bootstrapped data sets and the programs SEQBOOT, DNADIST and CONSENSE of the PHYLIP package Felsenstein, supra.

Nucleotide sequence accession numbers

The 16S rRNA gene sequence determined in this study is deposited with GenBank under accession number AF181848. The accession numbers and strain designations of the reference 16S rRNA gene sequences used in the phylogenetic analyses are as follows: *Anaerobranca horikoshii* DSM 9786$^T$ (U21809), *Caldicellulosiruptor saccarolyticus* ATCC 43494$^T$ (L09178), *Caloramator coolhaasii* DSM 12679 AF104215, *Caloramator fervidus* ATCC 432045$^T$ (L09187), *Caloramator indicus* ACM 3982$^T$ (X75788), *Caloramator proteoclasticus* DSM 10124$^T$ (X90488), *Clostridium butyricum* ATCC 19398$^T$ (M59085), *Clostridium perfringens* ATCC 13124$^T$ (M59103), *Moorella glycerini* DSM 11254$^T$ (U82327), *Moorella thermoacetica* LJD$^T$ (M59121), *Moorella therrnoautotrophica* DSM 1974$^T$ (L09168), *Oxobacter pfennigii* DSM 3222$^T$ (X77838), *Thermoanaerobacter ethanolicus* ATCC 31550$^T$ (L09162), *Thermoanaerobacterium thermosulfurigenes* ATCC 3374$^T$ (L09171), *Thermobrachium celere* DSM 8682 X99238, *Thermosyntropho lipolytica* DSM 11003$^T$ (X99980).

Results

Enrichment and isolation

The basal medium containing glycerol was inoculated with approx. 10% (w/v) of the sample and incubated at 60° C. In addition medium of the same composition exhibiting pH 7.5 and pH 9.0 was inoculated with the sample (10% (w/v) each). Only at pH 6.0 an enrichment culture was obtained that utilized glycerol. After subsequent transfers (10% v/v), dilution series of this enrichment culture were prepared and plated out on solid basal medium (1.5% agar) using soft agar overlays, which consisted of basal medium containing 0.8% agar. Single colonies were picked, subcultured in liquid medium of the same composition and formation of 1,3-propanediol was determined by HPLC. For subsequent platings, the procedure was repeated several times using basal medium as well as defined complex medium described by Kell et al., *Biochem. Biophys. Res. Commun.* 99:81–88 (1981). Growth in liquid medium was largely enhanced when the cultures were incubated under shaking. After transferring colonies into liquid basal media at 60° C. under shaking, a glycerol-fermenting culture was obtained, which was considered as pure and was designated as strain JW/MS-VS5$^T$.

Colony and cell morphology

On plates containing basal medium the colonies appeared after 7–10 days. Once adapted to growth on plates, subsequent streaks on fresh plates yielded colonies after 2–3 days. The colonies were uniformly round, white and 1.0 to 1.5 mm in diameter. Cells of strain JW/MS-VS5$^T$ were straight to slightly curved rods, 0.4 to 0.6 m in diameter and 2.0 to 3.0 m in length. The cells occurred mostly single. No indication of motility was obtained by using light microscopy. Electron microscopy analysis performed after negative staining did not reveal the presence of flagella, using cells from different growth stages. The occurrence of spores was not observed at any growth stage.

Gram-staining reaction and Gram type

The cells stained Gram positive only in the early exponential growth phase. Ultrathin sections of strain JW/MS-VS5$^T$ revealed a thick peptidoglycan, thus the organism was regarded as Gram type positive Wiegel, *Int. J. Syst. Bacteriol.*, 47:651–56 (1997). This placement is consistent with the 16S rRNA sequencing data which placed the organism in the Clostridium-Bacillus branch. In addition to the peptidoglycan, another outer layer was observed, which might represent an S-layer, however EM micrographs failed to reveal any geometrical arrays.

Temperature and pH ranges

Figure 2:
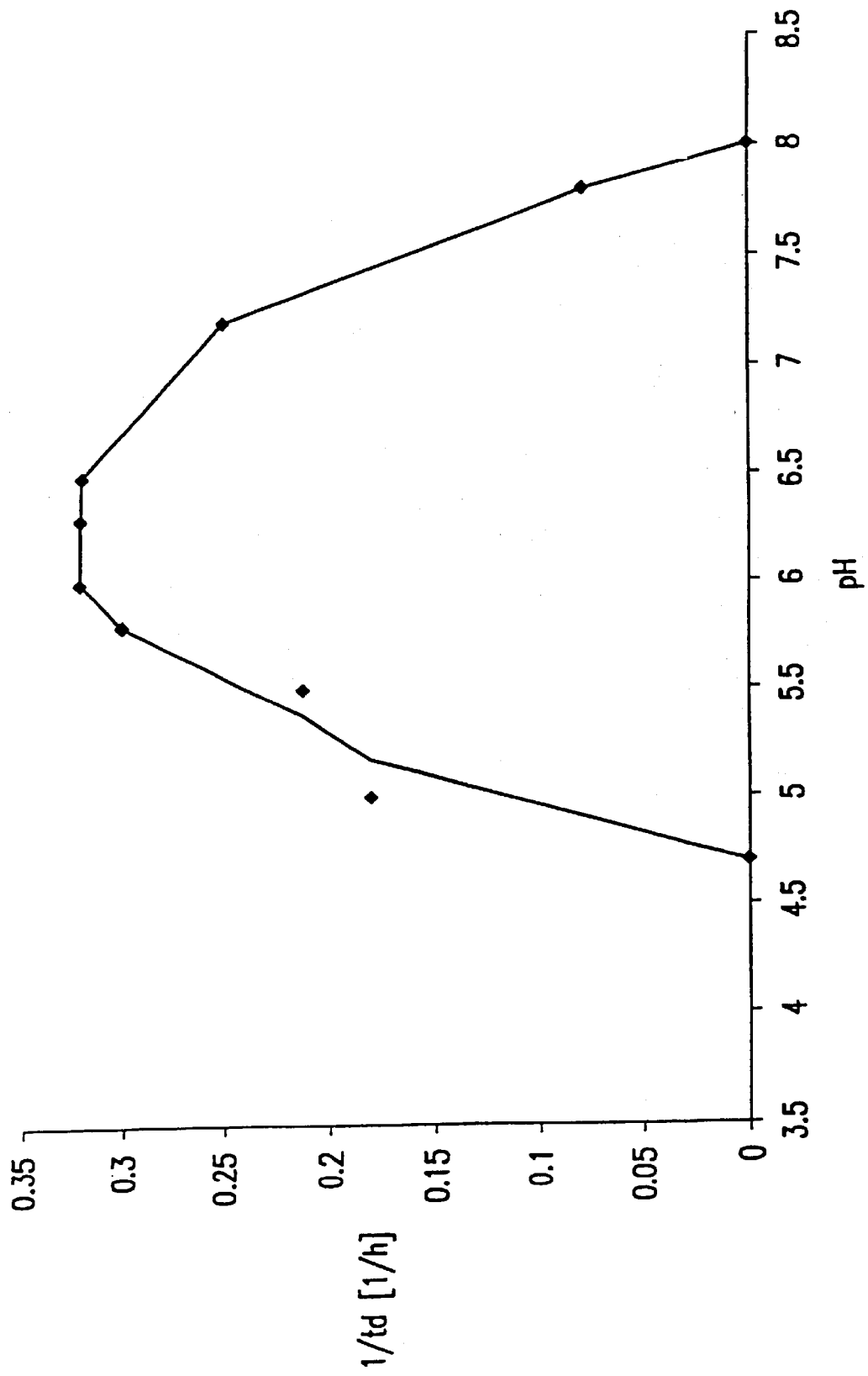
FIG. 2 shows effect of pH$^{25C}$ on growth of strain JW/MS-VS-5 at 60° C., td=doubling time.

The temperature range at $pH^{25C}$ 6.0 for growth of strain JW/MS-VS5$^T$ was from 33 to 64° C. with an optimum at 58° C. (FIG. 1). No growth was detected at 67° C. or at temperatures lower than 33° C. The strain grew in a $pH^{25C}$ range from 5.0 to 7.8, with an optimum at $pH^{25C}$ 6.0–6.5 (FIG. 2). No growth was detected at $pH^{25C}$ 4.7 and $pH^{25C}$ 8.0. The shortest doubling time under optimal conditions was 2.8 h.

Substrate utilization and fermentation products

The substrates utilized included glycerol, glucose, fructose, sucrose, cellobiose, lactose, galactose, mannose (20 mM), starch and yeast extract (5 g/l). Strain JW/MS-VS5$^T$ did not use xylose, arabinose, acetate, lactate, formate, methanol, ethanol, n-propanol, i-propanol, n-butanol, propionate, acetone, succinate, ethylene glycol, 1,2-propanediol, phenol, benzoate and $H_2/CO_2$.

As shown in Table 1, fermentation of glycerol yielded acetate and 1,3-propanediol as the only organic metabolic products. No $C_1$–$C_3$ alcohols, diols other than 1,3-propanediol or organic acids other than acetate were detected in measurable amounts. Significant amounts of $H_2$ were produced in these cultures.

The obtained fermentation pattern suggests a conversion of glycerol according to the following equation: 3 Glycerol→2 1,3-Propanediol+Acetate+$CO_2$+$H_2$.

Electron acceptors

In the presence of glycerol as a substrate, strain JW/MS-VS5$^T$ did not reduce nitrate (10 mM), amorphous Fe(III) oxide (90 mM), 9,10-anthraquinone-2,6-disulfonic acid (AQDS), sulfate (10 mM), or precipitated or sublimed $S_o$ (30 mM). Production of 1,3-propanediol was not effected in the presence of any of these electron acceptors. Strain JW/MS-VS5$^T$ was not capable of growth with $O_2$ (20% v/v) in the gas phase.

Antibiotic susceptibility

Ampicillin, chloramphenicol, erythromycin, rifampicin, and kanamycin completely inhibited growth at a concentration of 100 mg/ml of medium. Addition of streptomycin and tetracyclin of the same concentration resulted in retardation of growth.

DNA base composition

The G+C content of the genomic DNA was 32 mol % (HPLC).

16S rRNA gene sequence comparison

Figure 3:
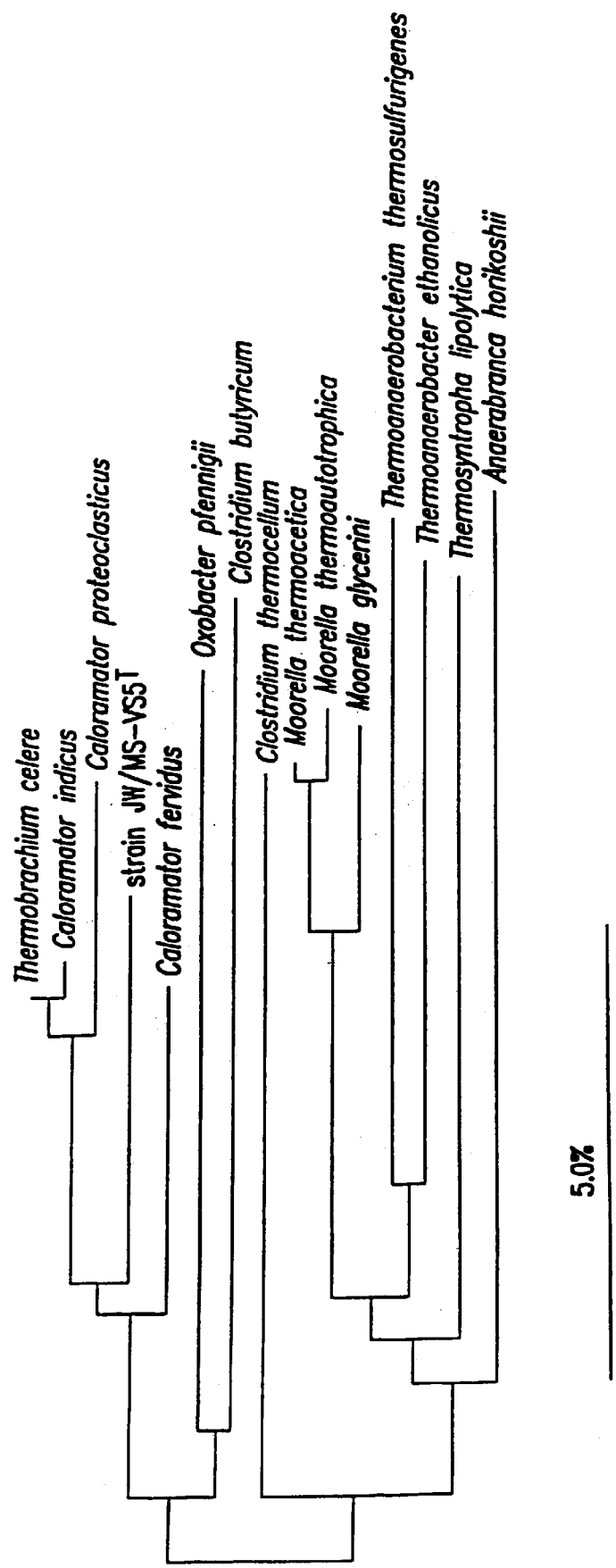
FIG. 3 shows an unrooted phylogenetic dendrogram based on a comparison of the 16S rRNA gene sequences of JW/MS-VS-5 and related strains. The neighbor-joining tree was reconstructed from distance matrices. Bootstrap values from the analyses of 1000 data sets (expressed as percentages) are shown at the branching points. The scale bar represents nucleotide substitutions per 100 nucleotides.
Figure 5:
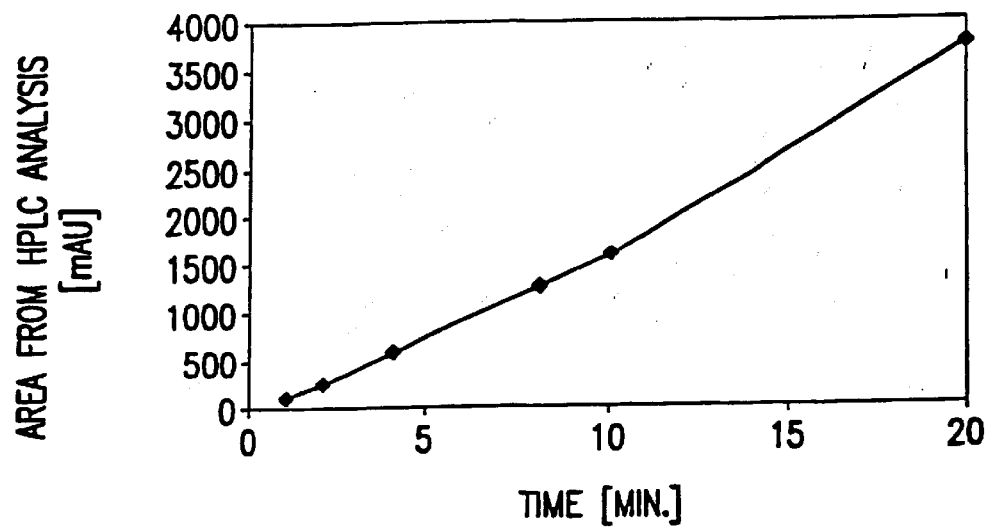
FIG. 5 shows a time course assay for the conversion of 1,2-propanediol to propionaldehyde by anaerobically toluenized JW/MS-VS-5 cells at 60° C. under anaerobic conditions.

An almost complete 16S rRNA gene sequence of strain JW/MS-VS5 comprising 1480 nucleotides in length was determined. Two data sets were used for the phylogenetic analyses. Data set one contained the sequence determined in this study and a selection of reference sequences from the low G+C Gram positive bacteria while data set two contained the new sequence and the sequences available in the databases for the five species of the genera Caloramator and Thermobrachium. Phylogenetic analyses based on data set one comprising 1206 unambiguous nucleotides between positions 98 and 1469 (E. coli positions, Brosius et al., Proc. Natl. Acad. Sci. USA 75:4801–4805 (1978)) showed the new isolate to cluster together as distinct lineage within the radiation of the previously described genera Caloramator and Thermobrachium (FIG. 3). Strain JW/MS-VS5 shares 91.7 to 94.1% 16S rRNA gene sequence similarity with species of the previously described genera Caloramator and Thermobrachium and between 83.4 and 87.1% similarity to the sequences of the other taxa included in data set one and shown in (FIG. 3). The second data set containing the sequences of the new isolate and those of the five other Caloramator and Thermobrachium species and comprising 1393 unambiguous nucleotides between positions 38 and 1469 (E. coli positions, Brosius et al., above) was used to calculate pairwise similarity values between the taxa of this cluster. The 16S rRNA gene sequence similarities between strain JW/MS-VS5 and the previously described taxa were in the range 91.3 to 93.7%. Within the Caloramator/Thermobrachium cluster the highest sequence similarity value (93.7%) was found between strain JW/MS-VS5 and Thermobrachium celere. Bootstrap analyses on the branches recovered in FIG. 5 clearly give support to the Caloramator/Thermobrachium cluster and the relationship of this group to the genus Clostridium cluster I as defined in Collins et al., Int. J. Swiss P. Bacteriol. 44:812–826 (1994).

As is apparent from the phylogenetic analysis (FIG. 3), the strain is closest related to Thermobrachium celere and three Caloramator species that form a distinct cluster within the Gram-type positive Bacillus-Clostridium branch of the phylogenetic tree. These four species are thermophilic, chemoorganoheterotrophic anaerobic bacteria exhibiting a low G+C content, which applies for strain JW/MS-VS5$^T$ as well. Table 2 shows a comparison of morphological and physiological traits of the five species found in this cluster.

TABLE 1

Fermentation of glycerol by strain JW/MS-VS5$^T$

| Substrate | Product formed [mM] | | | Carbon |
|---|---|---|---|---|
| Glycerol consumed [mM] | 1,3-Propanediol | Acetate | $H_2$ | recovery [%] |
| 16.2 | 11.2 | 4.8 | 6.5 | 99 |

The initial concentration of glycerol used for cultivation of strain JW/MS-VS5$^T$ in basal medium was 33 mM.

TABLE 2

Selected properties of strains used in this study: JW/MS-VS5$^T$, Thermobrachium celere, and Caloramator species C. fervidus, C. indicus, and C. proteoclasticus.

| | Property | | | | | | |
|---|---|---|---|---|---|---|---|
| Strain | Spore Formation | Temperature Range | Temperature Optimum | pH optimum | Utilization of glycerol | Shortest doubling time [h] | G + C content [mol %] |
| JW/MS-VS5$^T$ | – | ≧33–≦64 | 58 | 6.0–6.5 | + | 2.80 | 32 |
| T celere* | – | >(37–45)– <(70–80) | 62–67 | 8.0–8.5 | – | 0.17 | 30–31 |

TABLE 2-continued

Selected properties of strains used in this study: JW/MS-VS5$^T$, Thermobrachium celere, and Caloramator species C. fervidus, C. indicus, and C. proteoclasticus.

| Strain | Spore Formation | Temperature Range | Temperature Optimum | pH optimum | Utilization of glycerol | Shortest doubling time [h] | G + C content [mol %] |
|---|---|---|---|---|---|---|---|
| C. indicus | − | >37–<80 | 60–65 | 8.1 | NR | 0.33 | 25 |
| C. fervidus | + | >37–<80 | 68 | 7.0–7.5 | NR | 0.75 | 39 |
| C. proteo-clasticus | + | ≦30–<68 | 55 | 7.0–7.5 | NR | 0.50 | 31 |

NR: not reported
*: different strains

EXAMPLE
Detection of a dhaB-like Gene in JW/MS-VS5$^T$
Materials and Methods JW/MS-VS5$^T$ was characterized by a PCR method using the K. pneumoniae dhaB gene as a positive control. Four sets of primers were used: (a) dhaB1, consisting of dhaB15' GGA ATT CAG ATC TCA GCA ATG AAA AGA TCA AAA CG (SEQ ID NO:1) and dhaB13' GCT CTA GAT TAT TCA ATG GTG TCG GG (SEQ ID NO:2); (b) dhaB2, consisting of dhaB25' GGA ATA CAG ATC TCA GCA ATG CAA CAG ACA ACC C (SEQ ID NO:3) and dhaB23' GCT CTA GAT CAC TCC CTT ACT AAG TCG (SEQ ID NO:4); (c) dhaB3, consisting of dhaB35' GGA ATT CAG ATC TCA GCA ATG AGC GAG AAA ACC ATG C (SEQ ID NO:5) and dhaB33' GCT CTA GAT TAG CTT CCT TTA CGC AGC (SEQ ID NO:6); and (d) dhaX, consisting of dhaX5' AGG TGG TGC GGA TCC TGT CGA ATC CCT A (SEQ ID NO:7) and dhaX3' GAT ACG AGA TCT TTA ATT CGC CTG ACC GGC CAG TAG CAG (SEQ ID NO:8). All primers were purchased from GIBCO BRL. The PCR reaction was carried out in Hot Start PCR tubes (Molecular Bio-Products, Inc.) with 100 μl of PCR reaction reagents. Each 100 μl of PCR reaction contains: 2 ul of bacteria culture, 20 ul 1 mM dNTPs, 10 ul of 10× PCR buffer (100 mM KCL, 100 mM (NH4)2SO4, 200 mM Tris-CL (pH8.75), 20 mM MgSO4. 1% Triton, 1 mg/ml BSA)—[Stratagene, La Jolla, Calif.], 3 ul of each 2 opposing primer set (10 O.D./ul), and 1 ul Pfu DNA Polymerase (2.5 U/ul)—[Stratagene, La Jolla, Calif.] PCR amplifications were performed in an automated thermal MiniCycler (MJ Research) at three different annealing temperature to test the best condition. The final condition is as following: Five initial cycles of denaturation (94 C., 1.5 mm.), low stringency annealing (37 C., 1.5 mm.), and extension (72 C., 2.5 mm.). After initial cycles. 25 additional cycles at higher annealing stringency were conducted: denaturation (94 C., 1.5 mm.). annealing (55 C., 1.5 mm.), and extension (72 C., 2.5 mm.). Ten μl of 10×DNA loading dye was added to each sample and 15 μl of each PCR products were electrophoresed on an agarose gel.

Results

The positive control give the proper bands as expected. The unknown microorganism showed faint DNA bands with same size of dhaB 1 and dhab3 but not on dhaB2 and dhaX. The faint bands may be due to low homology of PCR primers and target genes. These results suggested that JW/MS-VS-5$^T$ may harbor a dhaB-like gene which serves the same or similar function as dhaB in K. pneumoniae.

EXAMPLE
In vitro Determination of JW/MS-VS5$^T$ Glycerol Dehydratase Activity Toluene-treated cells of strain JW/MS-VS5$^T$ were tested for the ability to convert glycerol to 3-hydroxypropionaldehye (3-HPA) and 1,2-propanediol to propioinaldehyde.

Materials and Methods

Cells were grown anaerobically at 60° C. in a mineral salts medium supplemented with 0.5 g/l yeast extract and 3 g/l glycerol, pH 6.8. Cells were harvested anaerobically and stored at −70° C. under nitrogen.

Frozen cells were thawed and treated with toluene in a glove box under anaerobic conditions. Toluene treatment consisted of the following steps: (a) washing the cells in 1 ml 50 mM $KPO_4$ pH 8.0; (b) spinning the cells 6 minutes at 14,000 RPM in an Eppendorf 5415C centrifuge; (c) washing the cells in 1.5 ml 50 mM $KPO_4$ pH 8.0; (d) again spinning the cells 6 minutes at 14,000 RPM in an Eppendorf 5415C centrifuge; (e) redissolving the cells in 2 ml 50 mM $KPO_4$ pH 8.0; (f) adding 20 μl toluene; (g) shaking vigorously for 15 minutes; (h) spinning the cells 10 minutes at 14,000 RPM in an Eppendorf 5415C centrifuge; (i) washing the cells in 2 ml 50 mM $KPO_4$ pH 8.0; (j) spinning the cells 6 minutes at 14,000 RPM in an Eppendorf 5415C centrifuge; (k) repeating steps (i) and (j); (l) redissolving the toluene-treated cells in 50 mM $KPO_4$ pH 8.0; (m) measuring the absorbance of the dissolved cells at 600 nm; and (n) storing the cells at −70° C.

Reaction mixtures contained in 1.0 ml: 15 mM $KPO_4$, pH 8.0; 0.25 M KCl; 200 mM glycerol or 1,2-propanediol; toluene-treated cells, 0.38 OD600; and 12 μM coenzyme $B_{12}$. Reactions were incubated at 60° C. anaerobically and samples were taken at times indicated on FIG. 4. 100 μl samples were added to 50 μl methyl benzyl thiazolinone hydrazone (MBTH) solution (6 mg/ml in 375 mM glycine-HCl pH 2.7), heated at 100° C. for 3 minutes, cooled on ice for 30 seconds, and clarified by centrifugation at 14K RPM for 5 minutes.

The clarified supernatants were then analyzed by detection of product on a $C_8$-reversed phase HPLC system as follows: (a) the column was a 15×4.6 cm Supelco, Supelcosil LC-8-DB, 3 μM particle size; (b) solvent A was 0.1% TFA; (c) solvent B was 90% acetonitrile, 0.08% TFA; (d) the gradient was (time[min.]/%B):0/0, 7/45, 17/65, 22/100, 24/100, 25/0, 30/0; (e) ejection volume was 20 μl; (f) injector draw speed was 833.3 μl/min; (g) detection was at 305 nm with a 500 nm reference; and (h) the bandwidth was 4 for sample wavelength and 80 for reference wavelength. Using this system, the retention time for 3-HPA was 8.7 min and for propionaldehyde was 10.7 min.

Results

Figure 4:
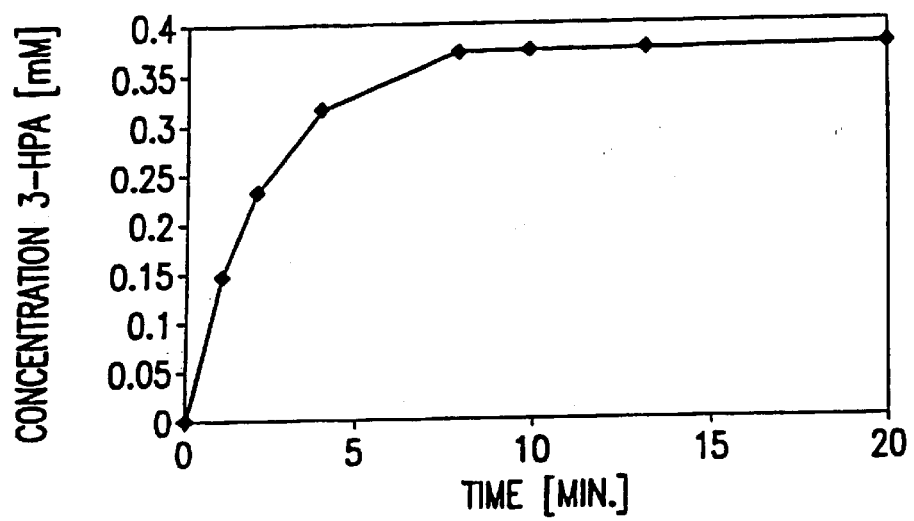
FIG. 4 shows a time course assay for the conversion of glycerol to 3-HPA by anaerobically toluenized JW/MS-VS-5 cells at 60° C. under anaerobic conditions.

The time courses for the conversion of glycerol to 3-HPA and 1,2-propanediol to propionaldehyde at 60° C. are shown in FIG. 4. The results indicate that glycerol dehydratase is active at 60° C., the growth temperature of the organism. The enzyme is inactivated by glycerol, but not 1,2-propanediol. Similar inactivation has been reported in the literature for other glycerol dehydratases. However, the glycerol dehydratase from Klebsiella is inactive at 60° C. Indeed, no glycerol dehydratase has been reported as active at 60° C.

Brief Description of Biological Deposit and Sequence Listing

*C. viterbiensis* type strain JW/MS-VS5$^T$ was deposited on Aug. 27, 1999 with the ATCC under the terms of the Budapest Treaty on the International Recognition of the Deposit of Micro-organisms for Purpose of Patent Procedure and is designated as ATCC PTA-584. "ATCC" refers to the American Type Culture Collection international depository located at 10801 University Boulevard, Manassas, Va. 20110-2209. The designations refer to the accession number of the deposited material.

The 16S rDNA sequence of strain JW/MS-VS5$^T$ was deposited in the Genbank database under accession number AF181848.

Equivalents

The foregoing written specification is sufficient to enable one skilled in the art to practice the invention. Indeed, various modifications of the above-described means for carrying out the invention which are obvious to those skilled in the field of molecular biology, biotechnology or related fields are intended to be within the scope of the following claims.

What is claimed is:

1. A method of converting glycerol to 1,3-propanediol in *Caloramator viterbiensis*, the method comprising culturing *Caloramator viterbiensis* that ferments glycerol to 1,3-propanediol under conditions such that 1,3-propanediol is produced, wherein said *Caloramator viterbiensis* is the organism deposited as ATCC designation PTA-584.

2. The method of claim 1, wherein the *Caloramator viterbiensis* is cultured at a pH between about 5.0 to about 7.8.

3. The method of claim 1, wherein the *Caloramator viterbiensis* is cultured at a pH between about 6.0 to about 6.5.

4.. The method of claim 1, wherein the *Caloramator viterbiensis* is cultured at a temperature between about 33° C. and about 64° C.

5. The method of claim 1, wherein the *Caloramator viterbiensis* is cultured at a temperature between about 50° C. and about 64° C.

6. The method of claim 1, wherein the *Caloramator viterbiensis* is cultured at a temperature between about 57° C. and about 64° C.

7. The method of claim 1, wherein the *Caloramator viterbiensis* is cultured at a pH of about 6.0 and a temperature of about 58° C.

8. The method of claim 1, wherein the *Caloramator viterbiensis* is cultured under anaerobic conditions.

9. The method of claim 1, wherein the *Caloramator viterbiensis* is cultured under nitrogen.

10. The method of claim 1, wherein the *Caloramator viterbiensis* is cultured under argon.

11. The method of claim 1, wherein the *Caloramator viterbiensis* is cultured under a mixture of nitrogen and carbon dioxide in a ratio of nitrogen to carbon dioxide of about 80 to about 20.

12. The method of claim 1, wherein the *Caloramator viterbiensis* is cultured in the presence of an oxygen scavenger.

13. The method of claim 1, wherein the *Caloramator viterbiensis* is cultured in an anaerobic chamber.

14. The method of claim 1, wherein the *Caloramator viterbiensis* is cultured under microaerobic conditions.

15. The method of claim 1, wherein the *Caloramator viterbiensis* is adsorbed on a solid support.

16. The method of claim 1, wherein the *Caloramator viterbiensis* is cultured under aerobic conditions.

17. A method of converting glycerol to 1,3-propanediol in *Caloramator viterbiensis*, the method comprising culturing *Caloramator viterbiensis*, wherein said *Caloramator viterbiensis* is the organism deposited as ATCC designation PTA-584 that ferments glycerol to 1,3-propanediol at a temperature between 33 and 64° C. and the pH of the medium being maintained between pH 6.0 and 6.5, such that 1,3-propanediol is produced.

18. A method of converting glycerol to 1,3-propanediol in *Caloramator viterbiensis,* the method comprising culturing *Caloramator viterbiensis,* wherein said *Caloramator viterbiensis* is the organism deposited as ATCC designation PTA-584 that ferments glycerol to 1,3-propanediol at a temperature between 50 and 64° C. and the pH of the medium being maintained between pH 6.0 and 6.5, such that 1,3-propanediol is produced.

19. A method of converting glycerol to 1,3-propanediol in *Caloramator viterbiensis,* the method comprising culturing *Caloramator viterbiensis,* wherein said *Caloramator viterbiensis* is the organism deposited as ATCC designation PTA-584 that ferments glycerol to 1,3-propanediol at a temperature between 57 and 64° C. and the pH of the medium being maintained between pH 6.0 and 6.5, such that 1,3-propanediol is produced.

* * * * *